(12) United States Patent
Jeong et al.

(10) Patent No.: US 9,670,412 B2
(45) Date of Patent: Jun. 6, 2017

(54) POLYSILSESQUIOXANE-DENDRON LIQUID CRYSTALS AND METHOD FOR PREPARING THE SAME

(71) Applicant: INDUSTRIAL COOPERATION FOUNDATION CHONBUK NATIONAL UNIVERSITY, Jeonju-si, Jeollabuk-do (KR)

(72) Inventors: Kwang Un Jeong, Jeonju-si (KR); Yun Bae Kook, Jeonju-si (KR); In Soo Kim, Jeonju-si (KR)

(*) Notice: Subject to any disclaimer, the term of this patent is extended or adjusted under 35 U.S.C. 154(b) by 0 days.

(21) Appl. No.: 14/650,291

(22) PCT Filed: Dec. 6, 2013

(86) PCT No.: PCT/KR2013/011257
§ 371 (c)(1),
(2) Date: Sep. 18, 2015

(87) PCT Pub. No.: WO2014/088362
PCT Pub. Date: Jun. 12, 2014

(65) Prior Publication Data
US 2016/0002537 A1    Jan. 7, 2016

(30) Foreign Application Priority Data
Dec. 7, 2012  (KR) .......................... 10-2012-0141563

(51) Int. Cl.
| | | |
|---|---|---|
| C07F 7/08 | (2006.01) | |
| C08G 77/04 | (2006.01) | |
| C09K 19/40 | (2006.01) | |
| G02F 1/133 | (2006.01) | |
| C09K 19/56 | (2006.01) | |
| C07F 7/21 | (2006.01) | |
| C09K 19/04 | (2006.01) | |

(52) U.S. Cl.
CPC ............... C09K 19/56 (2013.01); C07F 7/21 (2013.01); C09K 19/406 (2013.01); G02F 1/133 (2013.01); *C09K 2019/0418* (2013.01)

(58) Field of Classification Search
CPC .......... C07F 7/08; C08G 77/04; C09K 19/408; G02F 1/133
USPC ............... 528/33; 556/482; 428/1.1; 430/20; 349/2; 252/299.66
See application file for complete search history.

(56) References Cited

U.S. PATENT DOCUMENTS

| | | | |
|---|---|---|---|
| 6,277,451 B1 | 8/2001 | Mehl et al. | |
| 7,410,677 B2 * | 8/2008 | Hirai ................. | C09K 19/2007 252/299.01 |
| 2005/0224754 A1 | 10/2005 | Hirai et al. | |

* cited by examiner

*Primary Examiner* — Venkataraman Balasubramanian
(74) *Attorney, Agent, or Firm* — McClure, Qualey & Rodack, LLP

(57) ABSTRACT

Due to excellent processability of the POSS-dendron-structured liquid crystal compound according to the present invention, it is possible to coat and print on the compound and, also, to manufacture large size flexible devices.

According to the present invention, it is possible to maximize the physical bond strength between liquid crystals and, thus, to form higher-order structures by controlling the physical bond strength.

Since the POSS-dendron-structured liquid crystal compound of the present invention introduces non-functional groups to inorganic chemicals in contrast to the conventional liquid crystals, the compound disperses well into general types of solvents. In addition, the chemical and mechanical properties of the compound of the invention, such as increase of maximum allowable temperature, inhibition of oxidation, increase of surface hardness, etc., improves since polysilsesquioxane includes reactive or non-reactive organic compounds.

When the POSS-dendron-structured liquid crystal compound of the invention is used as an additive for liquid crystal layers, it can enhance the orientation of liquid crystal molecules. Moreover, the POSS part of the added liquid crystal compound of the invention may move to the lower surface of the liquid crystal layer and, then, improves the orientation.

16 Claims, 23 Drawing Sheets

[Chemical Formula 4]

[Chemical Formula 5]

[Table 3]

| | |
|---|---|
| Chemical Formula 29 | Chemical Formula 30 |
| Chemical Formula 31 | Chemical Formula 32 |
| Chemical Formula 33 | Chemical Formula 34 |
| Chemical Formula 35 | Chemical Formula 36 |
| Chemical Formula 37 | Chemical Formula 38 |
| Chemical Formula 39 | Chemical Formula 40 |

FIG. 6

[Table 4]

| | R1 | M | R2 | L1 |
|---|---|---|---|---|
| 1-1 | CH3(CH2)n- | -⬡-⬡- | -OCH2(CH2OCH2)nCH2O- | Chemical Formula 3-1 |
| 1-2 | CH3(CH2)n- | -⬡-⬡- | -OCH2(CH2OCH2)nCH2O- | Chemical Formula 3-2 |
| 1-3 | CH3(CH2)n- | -⬡-⬡- | -OCH2(CH2OCH2)nCH2O- | Chemical Formula 3-3 |
| 1-4 | CH3(CH2)n- | -⬡-⬡- | -OCH2(CH2OCH2)nCH2O- | Chemical Formula 3-4 |
| 1-5 | CH3(CH2)n- | -⬡-⬡- | -OCH2(CH2OCH2)nCH2O- | Chemical Formula 3-5 |
| 1-6 | CH3(CH2)n- | -⬡-⬡- | -OCH2(CH2OCH2)nCH2O- | Chemical Formula 3-6 |
| 1-7 | CH3(CH2)n- | -⬡-⬡- | -O(CH2)nO- | Chemical Formula 3-1 |
| 1-8 | CH3(CH2)n- | -⬡-⬡- | -O(CH2)nO- | Chemical Formula 3-2 |
| 1-9 | CH3(CH2)n- | -⬡-⬡- | -O(CH2)nO- | Chemical Formula 3-3 |
| 1-10 | CH3(CH2)n- | -⬡-⬡- | -O(CH2)nO- | Chemical Formula 3-4 |
| 1-11 | CH3(CH2)n- | -⬡-⬡- | -O(CH2)nO- | Chemical Formula 3-5 |
| 1-12 | CH3(CH2)n- | -⬡-⬡- | -O(CH2)nO- | Chemical Formula 3-6 |
| 1-13 | CH3(CH2)n- | -⬡-⬡- | -(CH2)n- | Chemical Formula 3-1 |
| 1-14 | CH3(CH2)n- | -⬡-⬡- | -(CH2)n- | Chemical Formula 3-2 |
| 1-15 | CH3(CH2)n- | -⬡-⬡- | -(CH2)n- | Chemical Formula 3-3 |
| 1-16 | CH3(CH2)n- | -⬡-⬡- | -(CH2)n- | Chemical Formula 3-4 |
| 1-17 | CH3(CH2)n- | -⬡-⬡- | -(CH2)n- | Chemical Formula 3-5 |
| 1-18 | CH3(CH2)n- | -⬡-⬡- | -(CH2)n- | Chemical Formula 3-6 |

FIG. 7A

[Table 4 (Continued)]

| | R1 | M | R2 | L1 |
|---|---|---|---|---|
| 2-1 | CH3(CH2)n- | -O-⬡-⬡-O- | -(CF2)n- | Chemical Formula 3-1 |
| 2-2 | CH3(CH2)n- | -O-⬡-⬡-O- | -(CF2)n- | Chemical Formula 3-2 |
| 2-3 | CH3(CH2)n- | -O-⬡-⬡-O- | -(CF2)n- | Chemical Formula 3-3 |
| 2-4 | CH3(CH2)n- | -O-⬡-⬡-O- | -(CF2)n- | Chemical Formula 3-4 |
| 2-5 | CH3(CH2)n- | -O-⬡-⬡-O- | -(CF2)n- | Chemical Formula 3-5 |
| 2-6 | CH3(CH2)n- | -O-⬡-⬡-O- | -(CF2)n- | Chemical Formula 3-6 |
| 2-7 | CH3(CH2)n- | -O-⬡-⬡-O- | -CH2(CH2OCH2)nCH2- | Chemical Formula 3-1 |
| 2-8 | CH3(CH2)n- | -O-⬡-⬡-O- | -CH2(CH2OCH2)nCH2- | Chemical Formula 3-2 |
| 2-9 | CH3(CH2)n- | -O-⬡-⬡-O- | -CH2(CH2OCH2)nCH2- | Chemical Formula 3-3 |
| 2-10 | CH3(CH2)n- | -O-⬡-⬡-O- | -CH2(CH2OCH2)nCH2- | Chemical Formula 3-4 |
| 2-11 | CH3(CH2)n- | -O-⬡-⬡-O- | -CH2(CH2OCH2)nCH2- | Chemical Formula 3-5 |
| 2-12 | CH3(CH2)n- | -O-⬡-⬡-O- | -CH2(CH2OCH2)nCH2- | Chemical Formula 3-6 |
| 2-13 | CH3(CH2)n- | -O-⬡-⬡-O- | -OCH2(CF2)nCH2O- | Chemical Formula 3-1 |
| 2-14 | CH3(CH2)n- | -O-⬡-⬡-O- | -OCH2(CF2)nCH2O- | Chemical Formula 3-2 |
| 2-15 | CH3(CH2)n- | -O-⬡-⬡-O- | -OCH2(CF2)nCH2O- | Chemical Formula 3-3 |
| 2-16 | CH3(CH2)n- | -O-⬡-⬡-O- | -OCH2(CF2)nCH2O- | Chemical Formula 3-4 |
| 2-17 | CH3(CH2)n- | -O-⬡-⬡-O- | -OCH2(CF2)nCH2O- | Chemical Formula 3-5 |
| 2-18 | CH3(CH2)n- | -O-⬡-⬡-O- | -OCH2(CF2)nCH2O- | Chemical Formula 3-6 |

FIG. 7B

POLYSILSESQUIOXANE-DENDRON LIQUID CRYSTALS AND METHOD FOR PREPARING THE SAME

TECHNICAL FIELD

The present invention relates to a liquid crystal compound of POSS-dendron structure and method for preparing the same. More particularly, the present invention a liquid crystal compound of POSS-dendron structure, of which processability is enhanced by formation of physical bonds between molecules.

BACKGROUND ART

Due to recent improvements in performance of liquid crystal display devices, their application extends to PC monitors and portable information terminals, and even to large TVs. Thus, in order to meet the need for low-cost and high-quality large liquid crystal display devices, it is essential to produce LCD devices with wide viewing angle, high brightness, fast response time and high contrast. In addition, liquid crystal compounds with excellent processability and flexibility are required as the enlargement of LCD devices advances rapidly.

Meanwhile, various physical bonds induce self-assembly of organic or inorganic molecules, as well as deliver biometric data through in vivo unimolecular self-recognition and form higher-order protein structure via continuous self-recognition, thereby being applied to develop supramolecular self-assembly. It has been pointed out that, in order to develop supramolecular self-assembly by using such physical bonds, synthesis of molecules should be easy enough for large-scale production and, also, physical bonds between molecules should be sufficiently strong. Moreover, molecular orientation must be secured and molecular recognition should be possible. Despite these problems, it is necessary to attempt to apply supramolecular self-assembly via such physical bonds. Especially, it is also needed to synthesize supramolecules with excellent liquid crystal orientation as well as processability.

[Reference: *Polymer Science and Technology* Vol. 20, No. 6, December 2009 "Supramolecular Self-Assembly Using Arrays of Hydrogen-Bonds" edited by In Young Song and Taiho Park]

DISCLOSURE

Technical Problem

The object of the present invention is to provide a novel supramolecular compound with physical bonds.

Another object of the present invention is to provide a liquid crystal compound with enhanced mechanical and chemical properties.

Further object of the present invention is to provide a liquid crystal compound with wide viewing angle, high brightness, and rapid response time to an electric field.

Technical Solution

One aspect of the invention relates to POSS-dendron-structured liquid crystal compound of the following chemical formula 1,

[Chemical Formula 1]

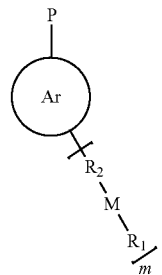

where Ar is $C_6$-$C_{20}$ arylene,
P is polysilsesquioxane,
$R_1$ and $R_2$ is independently $C_1$-$C_{30}$ hydrocarbon,
M is mesogen, and
m is 1-3.

Another aspect of the invention relates to a liquid crystal display (LCD) device comprising the liquid crystal compound.

Advantageous Effects

Due to excellent processability of the POSS-dendron-structured liquid crystal compound according to the present invention, it is possible to coat and print on the compound and, also, to manufacture large size flexible devices.

According to the present invention, it is possible to maximize the physical bond strength between liquid crystals and, thus, to form higher-order structures by controlling the physical bond strength.

Since the POSS-dendron-structured liquid crystal compound of the present invention introduces non-functional groups to inorganic chemicals in contrast to the conventional liquid crystals, the compound disperses well into general types of solvents. In addition, the chemical and mechanical properties of the compound of the invention, such as increase of maximum allowable temperature, inhibition of oxidation, increase of surface hardness, etc., improves since polysilsesquioxane includes reactive or non-reactive organic compounds.

When the POSS-dendron-structured liquid crystal compound of the invention is used as an additive for liquid crystal layers, it can enhance the orientation of liquid crystal molecules. Moreover, the POSS part of the added liquid crystal compound of the invention may move to the lower surface of the liquid crystal layer and, then, improves the orientation.

BRIEF DESCRIPTION OF THE DRAWINGS

FIG. 6 shows table 3.
FIGS. 7A-7B show table 4.

BEST MODE

The present invention may be carried out by the descriptions below. It should be understood that the following descriptions describe preferable embodiments of the invention and not limit the scope of the invention.

The invention relates to the POSS-dendron-structured liquid crystal compound of the following chemical formula 1,

[Chemical Formula 1]

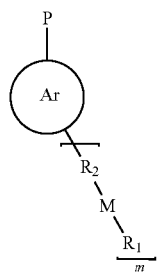

where Ar is $C_6$-$C_{20}$ arylene,
P is polysilsesquioxane,
$R_1$ and $R_2$ is independently $C_1$-$C_{30}$ hydrocarbon,
M is mesogen, and
m is 1-3.

Figure 1:
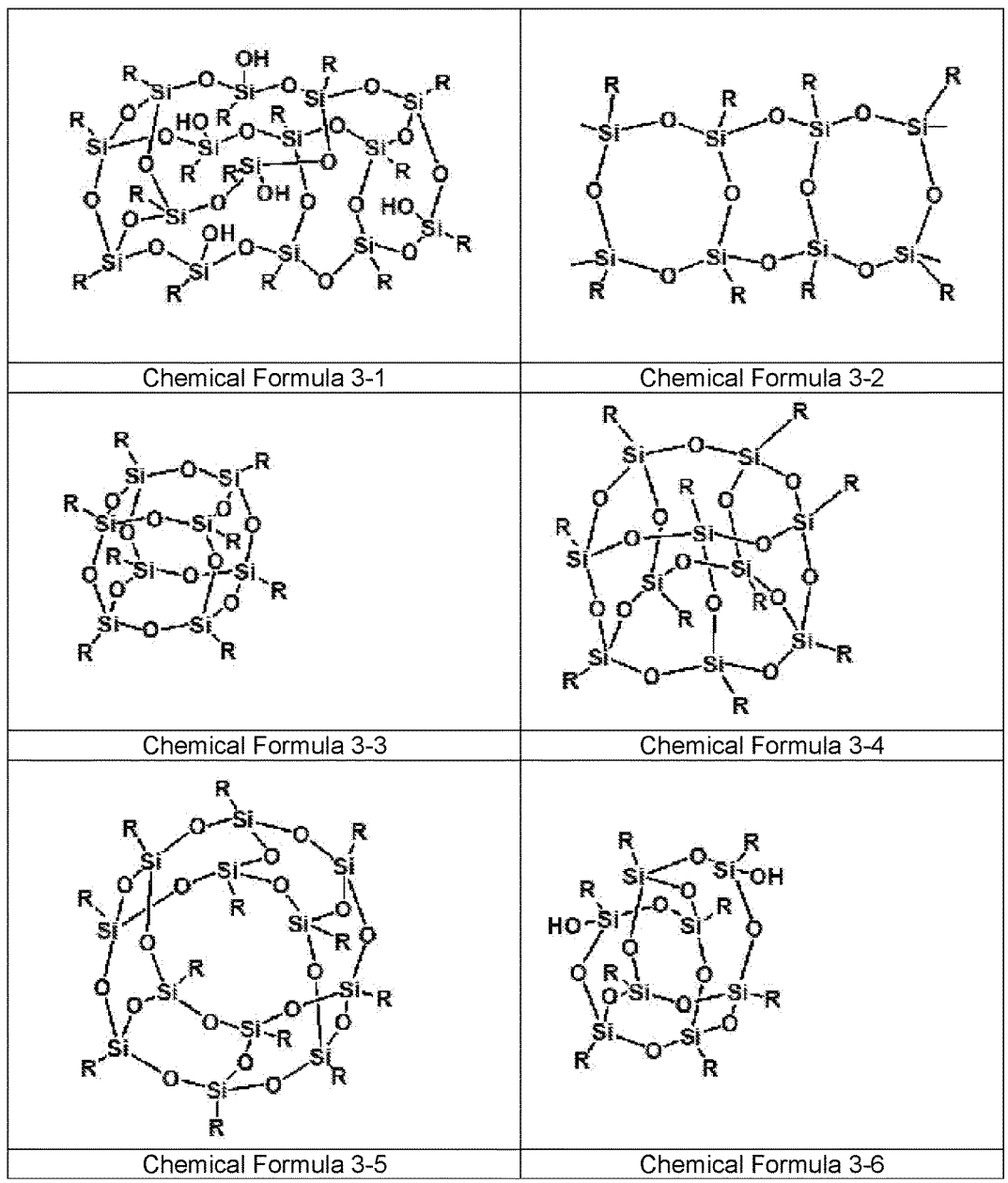
FIG. 1 shows chemical formula 3.

The polysilsesquioxane (POSS) may be indicated as the following chemical formula 2 (below) or 3 (see, FIG. 1):

[R—SiO$_{15}$]$_n$, [Chemical Formula 2]

where R is selected from the group consisting of $C_1$-$C_3$ alkyl, $C_1$-$C_3$ alkenyl, $C_3$-$C_{10}$ cycloalkyl, $C_6$-$C_{15}$ aryl, hydrogen and hydroxyl; and n is 3-1,000.

The molecular weight of the polysilsesquioxane is 500-100,000 g/mol.

Since the polysilsesquioxane exists as the chemical formula 1 having —(Ar)—[$R_2$-M-$R_1$]$_m$, the problem that it is difficult to disperse the POSS as a complex has be solved.

According to the present invention, the compound of the chemical formula 1 may be formed by introducing NCO to the end group of the POSS, followed by reacting —(Ar)—[$R_2$-M-$R_1$]$_m$ therewith, in order to bind —(Ar)—[$R_2$-M-$R_1$]$_m$ to the POSS.

In one embodiment of the present invention, the compound of the chemical formula 1 may be POSS-NHCOO—(Ar)—[$R_2$-M-$R_1$]$_m$ by binding of OH of Ar with NCO at the end of the POSS.

Although the compound of the chemical formula 1 contains POSS, the liquid crystal compound may disperse well at the level of molecule and, also, easily dissolve in organic solvents.

In addition, due to introduction of a polysilsesquioxane derivative, the polymeric properties, such as working temperature, inhibition of oxidation, surface hardness, mechanical properties, etc., of the liquid crystal compound of the chemical formula 1 are enhanced, and the combustibility, heat evolution and viscosity of the compound is reduced.

When the POSS-dendron-structured liquid crystal compound of the chemical formula 1 is used as an additive to the liquid crystal layer, the POSS moves to the lower surface of the liquid crystal layer and, then, enhances the orientation of the liquid crystal.

Figure 2:
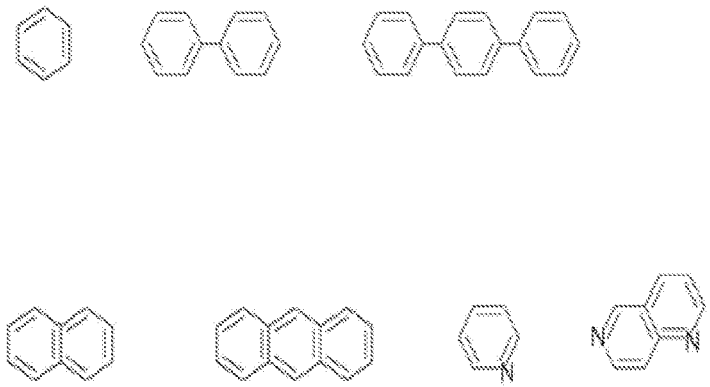
FIG. 2 shows chemical formula 4.

Ar of the chemical formula 1 is $C_6$-$C_{20}$ arylene and may include benzene ring compounds, fused benzene ring compounds and hetero ring compounds. At least one carbon atom of the Ar in the chemical formula 1 may be substituted by N, S or O which has non-covalent electron pair(s). Examples of the Ar may include the compounds of the chemical formula 4 (see, FIG. 2).

Figure 3:
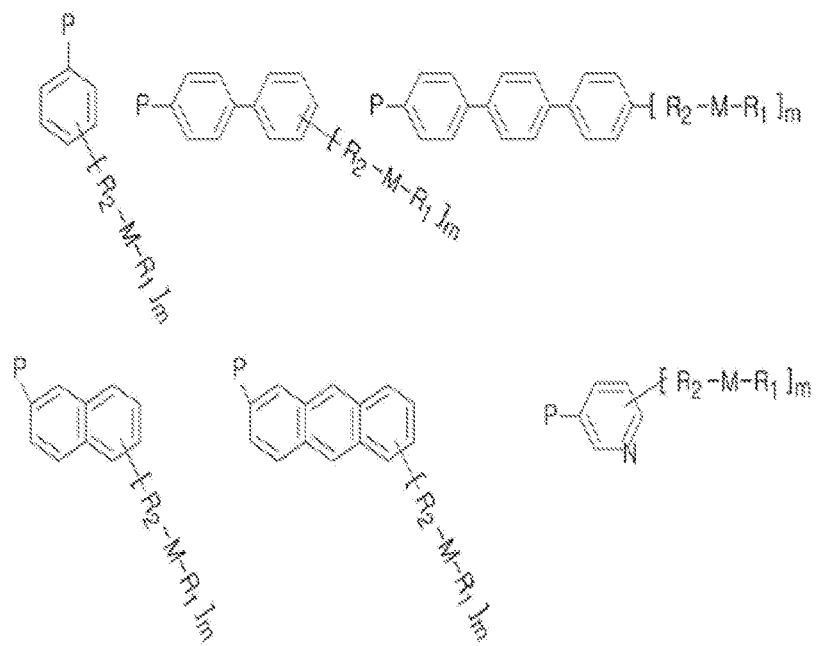
FIG. 3 shows chemical formula 5.

The chemical formula 1 may be indicated as the following chemical formula 5 (see, FIG. 3):

where P is polysilsesquioxane, $R_1$ and $R_2$ are independently $C_1$-$C_{30}$ hydrocarbon, M is mesogen, and m is 1-3.

$R_1$ and $R_2$ is independently $C_1$-$C_{30}$ hydrocarbon. At least one of $R_1$ and $R_2$ may be hydrophilic or hydrophobic. Preferably, any one of $R_1$ and $R_2$ is hydrophilic, the other is hydrophobic.

$R_1$ and $R_2$ are interchangeable with each other in the chemical formula 1.

$R_1$ and $R_2$ may be independently $C_2$-$C_{30}$ linear or branched alkyl, or $C_2$-$C_{30}$ alkenyl; or $C_2$-$C_{30}$ linear or branched alkyl, or $C_2$-$C_{30}$ alkenyl, of which at least one carbon atom is substituted by O, S, N or F.

$R_1$ and $R_2$ are independently $C_1$-$C_{30}$ alkylene, $C_1$-$C_{30}$ alkoxy, $C_1$-$C_{30}$ fluoroalkylene, $C_1$-$C_{30}$ ether, $C_1$-$C_{30}$ fluoroether or —O$R_3$O—, where $R_3$ may be $C_1$-$C_{30}$ alkylene or $C_1$-$C_{30}$ fluoroalkylene.

The mesogen may be indicated as the following chemical formula 6:

[Chemical Formula 6]

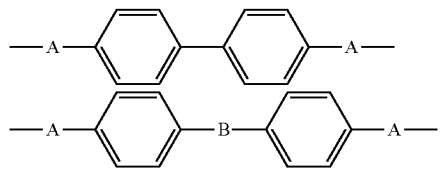

where A is —O—, —COO—, —OCO— or —NHCO—; B is S, O, $N_2$ or $(CH_2)_n$; and n is 1-20.

The mesogen itself has liquid crystallinity and excellent ability of self-assembly by π-π (interaction.

Figure 4:
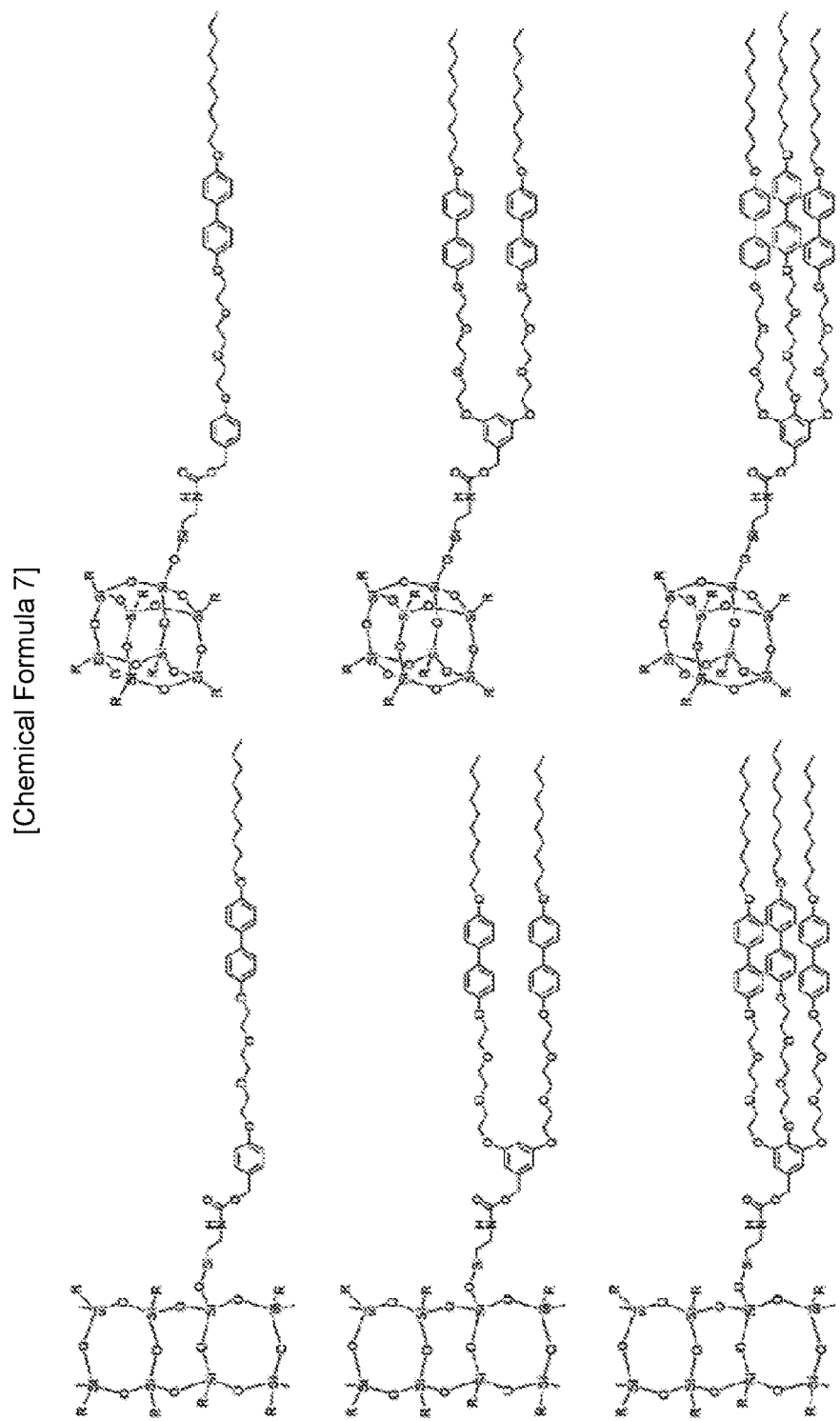
FIG. 4 shows chemical formula 7.

Examples of the POSS-dendron-structured liquid crystal compound may be indicated as the following chemical formula 7 (see, FIG. 4).

The weight average molecular weight of the POSS-dendron-structured liquid crystal compound may be 500-150,000 g/mol, preferably 500-3,000 g/mol.

The POSS-dendron-structured liquid crystal compound can form a physical bond between liquid crystals. The liquid crystal compound has many non-covalent electron pairs. For example, since carbon atoms in a hydrocarbon chain or an aromatic ring compounds are substituted by N, O, F or S, hydrogen bonds, π-π interactions, hydrophilic-hydrophobic intermolecular forces can be strengthened and, thereby, physical bonds between liquid crystals may be maximized. The dendron-structured compound may form a supramolecular structure by inducing physical bonds between liquid crystals.

Since the liquid crystal compound includes either of hydrophilic or hydrophobic hydrocarbon, or both of them, it has a wide range of selection for solvents and its processability is excellent. Furthermore, addition of the liquid crystal compound of the invention makes the interactions between the liquid crystal molecules increase, thereby allowing for a wider range of working temperature of the liquid crystal.

According to other aspect of the invention, the invention relates to an LCD device comprising the dendron-structured liquid crystal compound. Preferably, the LCD device of the invention may be applied to vertical alignment modes.

According to one embodiment of the invention, the liquid crystal display device of the invention may comprise a lower substrate with a pixel electrode and a common electrode which are arranged spacedly; a upper substrate arranged opposite to the lower substrate; a liquid crystal layer located between the upper substrate and the lower substrate, which is in an isotropic state without application of an electric field and in an anisotropic state with application of an electric field; and a polarizing plate crossing the upper substrate and the lower substrate.

The upper substrate, the lower substrate, the polarizing plate, the liquid crystal, etc., which are employed in the present invention may be manufactured by the known methods, materials and techniques.

For example, the lower substrate may be manufactured so as to comprise thin film transistors formed at each pixel on an insulating substrate and pixel electrodes connected to the transistors. In addition, the upper substrate plays a role in improvement of an image quality by forming black matrices out of opaque materials such as Cr, which substantially defines pixel-domains on an insulating plate, and is generally formed to overlap with the gates and/or data-lines of the lower substrate in order to reduce influence on an aperture ratio. The upper substrate comprises a color filter which is located below a black matrix and is corresponding to a pixel, and a common electrode formed on the color filter.

The liquid crystal may be a material that is optically isotropic with application of an electric field and optically anisotropic with application of an electric field, or that is optically anisotropic without application of an electric field and optically isotropic with application of an electric field, such as materials exhibiting the Pockels effect or the Kerr effect.

Examples of the liquid crystals which may be used for the present invention include 5CB (p-n-pentyl-p'-cyanobiphenyl), JC-1041 (Chisso), etc., and ZLI-4572 (Merck), ISO-(60BA)2, CB-15, etc. may be used as a chiral dopant.

The liquid crystal molecules of the LCD device of the invention aligns vertically. The liquid crystal may be used, of which dielectric anisotropy is negative when it is operated by using vertical electric field.

The POSS-dendron-structured liquid crystal compound may be used as an additive to a liquid crystal layer to enhance the alignment of the liquid crystal molecules. The dendron-structured liquid crystal compound may be employed 0.1-30 wt % relative to the liquid crystal.

When the dendron-structured liquid crystal compound is added to the liquid crystal layer, the POSS part of the liquid crystal may move to the lower surface of the liquid crystal layer and, then, enhance the orientation of the liquid crystal.

Detailed embodiments of the present invention will be described below, but not limiting the scope of the invention.

The chemical formula 8 shows examples of the POSS-dendron-structured liquid crystal compound which can be used for the invention.

[Chemical Formula 8]

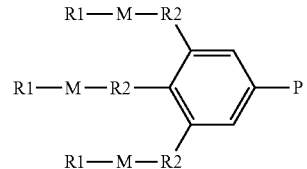

Figure 5:
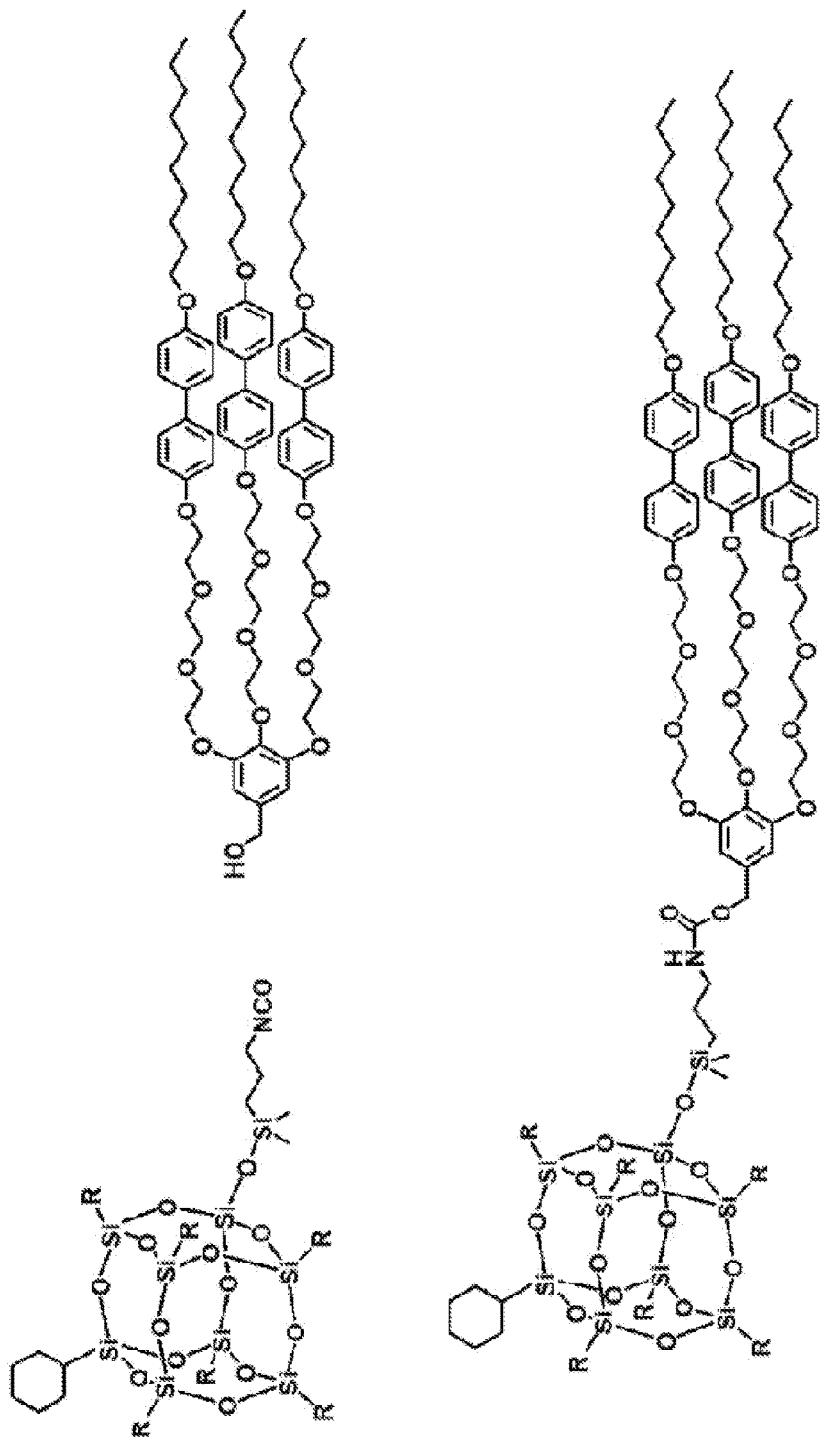
FIG. 5 shows reaction scheme 1.

One example of the method for preparing the POSS-dendron-structured liquid crystal compound of the chemical formula 8 will be described below. First, alkyl chain of $R_1$ and mesogen of M are reacted by weight ratio of 1:1.2 at 110° C. together with a catalyst of $K_2CO_3$ and a catalyst activator KI. Oxide chain of $R_2$ is mixed with tosyl group containing O by weight ratio of 1:2, together with a catalyst of trimethylamine and, then, reacted at room temperature. The reactants, $R_1$-M and $R_2$ are mixed by a weight ratio of 1:3 and reacted with addition of a catalyst of $K_2CO_3$ at 80° C. The thus obtained $R_1$-M-$R_2$ is mixed with benzoate containing three OH groups by a weight ratio of 1:5, followed by addition of a catalyst of $K_2CO_3$, and, after reaction at 80° C., $R_1$-M-$R_2$—Ar is formed. Subsequently, $R_1$-M-$R_2$—Ar and $LiAH_4$ are mixed by weight ratio of 1:10 to convert the end of Ar to $CH_2OH$. Lastly, the thus obtained $R_1$-M-$R_2$—Ar and polysilsesquioxane (molecular weight 1,159.99 g/mol) are mixed by a weight ratio of 1.2:1 and, then, reacted at 65° C. with addition of dibutyltin dilaurate as a catalyst to form liquid crystals containing POSS. The above reactions are shown in the following reaction scheme 1 (see, FIG. 5).

Examples of $R_1$ of the chemical formula 8 are listed in Table 1.

TABLE 1

| | | | |
|---|---|---|---|
| $CF_3(CF_2)_nCH_2CH_2OH$ | $CH_3(CH_2)_nBr$ | $CH_3(CH_2)_nOH$ | $CH_3(OCH_2CH_2)_nOH$ |
| Chemical Formula 9 | Chemical Formula 10 | Chemical Formula 11 | Chemical Formula 12 |
| $CH_3(OCH_2CH_2)_nBr$ | $CF_3(CF_2)_nBr$ | $CF_3(CF_2)_nI$ | $CF_3(CF_2)_nCH_2I$ |
| Chemical Formula 13 | Chemical Formula 14 | Chemical Formula 15 | Chemical Formula 16 |
| $CF_3(CF_2)_nCH_2OH$ | $CF_3(CF_2)_nCH_2CH_2I$ | $CH_3(CH_2)_nCl$ | |
| Chemical Formula 17 | Chemical Formula 18 | Chemical Formula 19 | | n is 1-20 in the chemical formulas 9-19.

n is 1-20 in the chemical formulas 9-19.

The OHs of the chemical formulas 9, 11, 12 and 17 can be substituted by tosylate.

$R_2$ of the chemical formula 8 can be selected from the groups listed in Table 2.

TABLE 2

| | | | |
|---|---|---|---|
| $Cl(CH_2)_nCl$ | $Br(CH_2)_nBr$ | $HO(CH_2)_nOH$ | $ClCH_2(CH_2OCH_2)_nCH_2Cl$ |
| Chemical Formula 20 | Chemical Formula 21 | Chemical Formula 22 | Chemical Formula 23 |
| $Cl(CF_2)_nCl$ | $I(CF_2)_nI$ | $Br(CF_2)_nBr$ | $HOCH_2(CH_2OCH_2)_nCH_2OH$ |
| Chemical Formula 24 | Chemical Formula 25 | Chemical Formula 26 | Chemical Formula 27 |
| $HOCH_2(CF_2)_nCH_2OH$ | | | |
| Chemical Formula 28 | | | | n is 1-12 in the chemical formulas 20-28.

Either or both of OH of the chemical formulas 22, 27 and 28 can be substituted by tosylate.

M can be selected from the groups listed in Table 3 (see, FIG. 6).

$R_1$ and $R_2$ of the chemical formulas 29-40 may bind to M at m- or p-site.

1-8 nitrogen atoms may be present at the m- or p-site.

In addition, C1-C8 alkyl, instead of hydrogen, may be present at at the m- or p-site.

Detailed embodiments of the derivatives of the chemical formula 8 of the invention is listed in Table 4 (see, FIG. 7), but not limited thereto.

n of Table 4 may be determined by reference to the above-mentioned description.

Example 1

Synthesis of 3,4,5-tris[2-(2-{2-[4-(4'-octyloxy)hydroxy-biphenyl]ethoxy}ethoxy)ethoxy]benzoic acid methyl ester 1-bromooctane (11.7 g, 6058 mmol) and 4,4-biphenol (13.54 g, 72.70 mmol) were added to purified N,N-dimethylformamide (DMF, 80 mL) in a 250 mL 1 neck round flask. Then, potassium carbonate (8.37 g, 60.58 mmol) and potassium iodine (1.01 g, 6.06 mmol) were added, followed by reflux at 110° C. for 12 hr. After reaction, the reaction products and 1,000 mL of water were poured to a 2,000 mL beaker and agitated, followed by filtration. Thereafter, the residue was dissolved by ethyl acetate and, then, filtered. The filtered solvent was evaporated. The thus obtained product was recrystallized by using 150 mL of ethanol. Finally, the product was obtained by filtration. (yield=7.86 g, 43%)

Figure 8:
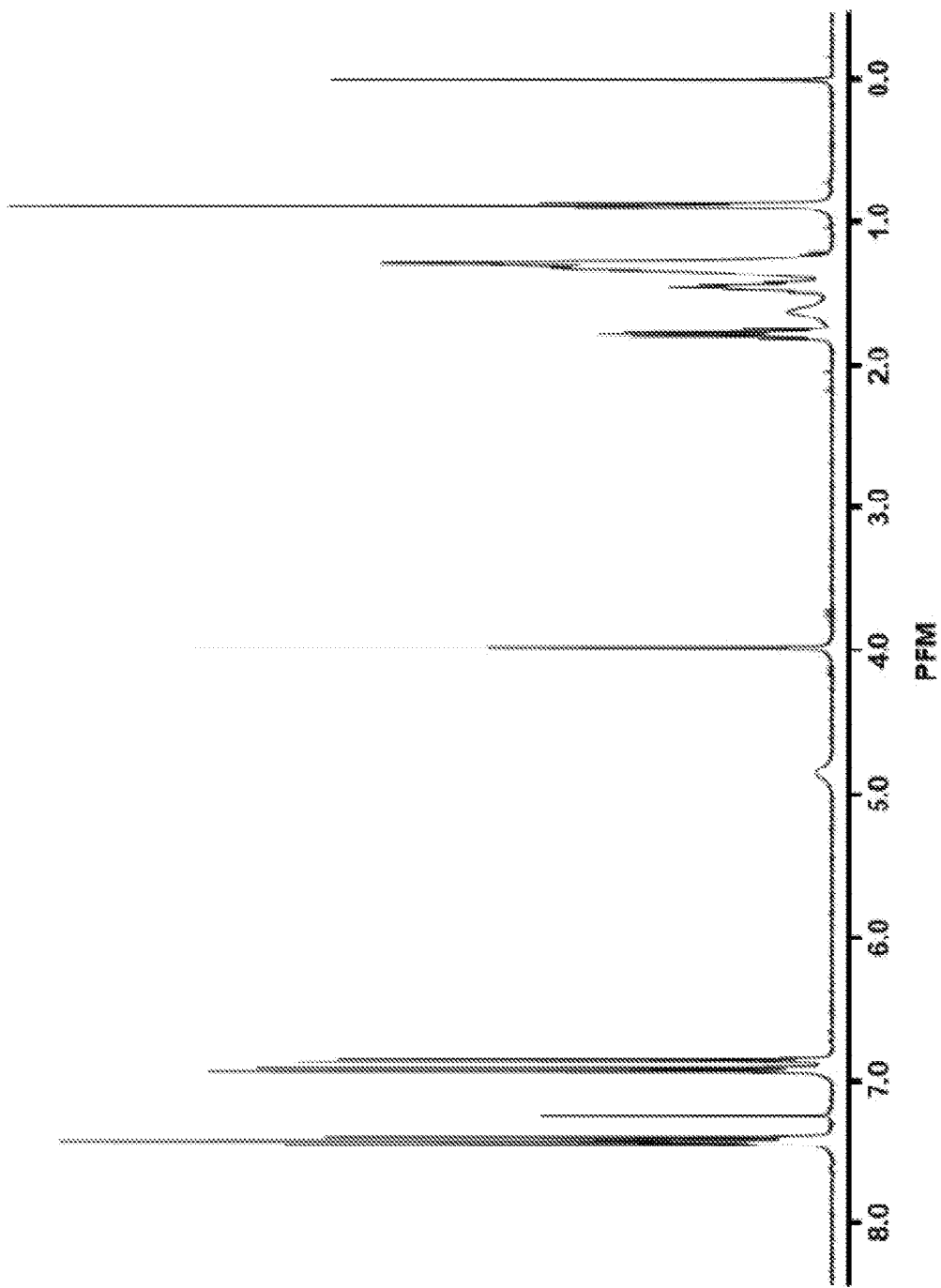
FIG. 8 shows the synthesis of 3,4,5-tris[2-(2-{2-[4-(4'-octyloxy)hydroxybiphenyl]ethoxy}ethoxy)ethoxy]benzoic acid methyl ester.

$^1$H NMR (400 MHz, CDCl$_3$): δ 7.45-7.41 (t, 4H), 6.95-6.88 (dd, 4H), 4.72 (s, 1H), 4.00-3.96 (t, 2H), 1.83-1.76 (m, 2H), 1.50-1.25 (m, 10H), 0.90-0.87 (t, 3H). (See, FIG. 8).

Synthesis of tri(ethylene glycol) bis(p-toluenesulfonate)

p-toluenesulfonyl chloride (40.63 g, 213.09 mmol) was dissolved in methylene chloride (MC, 150 mL) in a 500 mL 1 neck round flask and, then, triethyleneglycol (16 g, 105.55 mmol) and triethylamine (29.72 mL, 213.09 mmol) were added. The reacting mixture was stirred at room temperature for 8 hr. After reaction, 200 mL of distilled water was added and extraction was carried out by using 600 mL of chloroform (CHCl$_3$). After removing the solvents, products were separated by column chromatography (silica, hexane/ethyl acetate=1:1 (v/v)). (yield=42.59 g, 87%)

Figure 9:
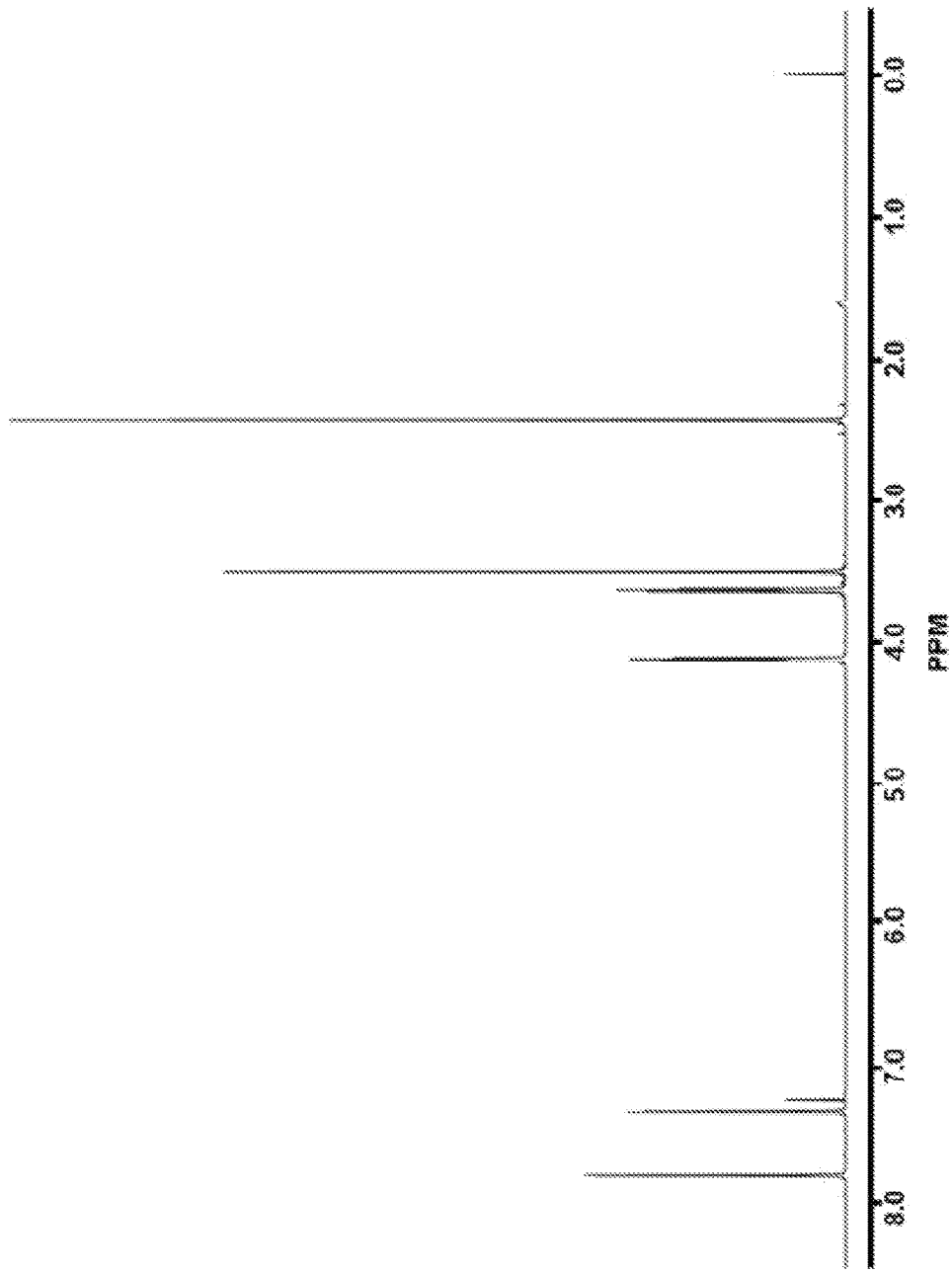
FIG. 9 shows the synthesis of tri(ethylene glycol) bis(p-toluenesulfonate).

$^1$H NMR (400 MHz, CDCl$_3$): δ 7.80-7.78 (d, 4H), 7.35-7.33 (d, 4H), 4.15-4.12 (t, 4H), 3.66-3.64 (t, 4H), 3.52 (s, 4H), 2.44 (s, 6H). (See, FIG. 9).

Synthesis of 2-(2-{2[4-(4'-octyloxy)hydroxybiphe-nyl]ethoxy}ethoxy)ethyl p-toluenesulfonate 4-(4'-octyloxy)-hydroxybiphenyl (4.88 g, 16.35 mmol) and tri(ethylene glycol) bis(p-toluenesulfonate) (22.50 g, 49.06 mmol) were dissolved in purified N,N-dimethylformamide (DMF, 150 mL) in a 500 mL 1 neck round flask and, then, potassium carbonate (9.04 g, 65.41 mmol) was added. The reaction mixture was refluxed at 80° C. for 5 hr. After removing the solvent, 200 mL of distilled water was added and extraction was carried out by using 600 mL of chloroform. After removing all the solvents, products were separated by column chromatography (silica, hexane/ethyl acetate=1:1 (v/v)) followed by another column chromatography (silica, methylene chloride/ethyl acetate=12:1, (v/v)). (yield=4 g, 42%)

Figure 10:
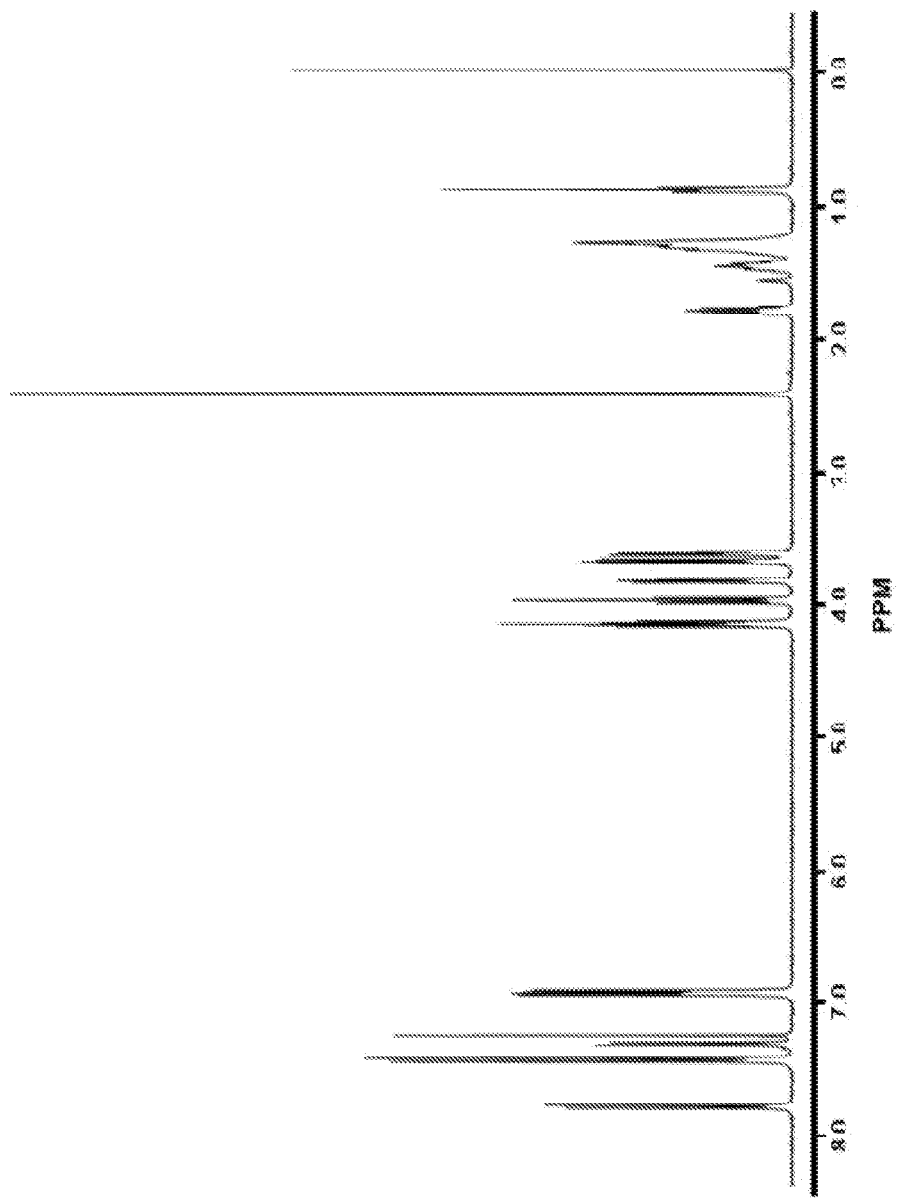
FIG. 10 shows the synthesis of 2-(2-{2-[4-(4'-octyloxy)hydroxybiphenyl]ethoxy}ethoxy)ethyl p-toluenesulfonate.

$^1$H NMR (400 MHz, CDCl$_3$): δ 7.80-7.78 (d, 2H), 7.4-7.44 (d, 4H), 7.32-7.30 (d, 2H), 6.96-6.93 (m 4H), 4.17-4.12 (m, 4H), 3.99-3.96 (t, 2H), 3.85-3.82 (t, 2H), 3.71-3.60 (m, 6H), 2.42 (s, 3H), 1.83-1.76 (m, 2H), 1.50-1.29 (m, 10H), 0.90-0.87 (t, 3H). (See, FIG. 10).

Synthesis of 3,4,5-tris[2-(2-{2-[4-(4'-octyloxy)hy-droxybiphenyl]ethoxy}ethoxy)ethoxy]benzoic acid methyl ester 2-(2-{2-[4-(4'-octyloxy)-hydroxybiphenyl] ethoxy}ethoxy)ethyl p-toluenesulfonate (4.03 g, 6.89 mmol) was dissolved in purified N,N-dimethylformamide (DMF, 40 mL) and, then, methy-3,4,5 trihydroxybenzoate (0.25 g, 1.38 mmol) and potassium carbonate (0.76 g, 5.51 mmol) were added. The reaction mixture was refluxed at 80° C. for 3 days under nitrogen atmosphere. After removing the solvent, 200 mL of distilled water was added and extraction was carried out by using 600 mL of chloroform. After removing the solvent, products were separated by column chromatography (silica, chloroform/ethyl acetate=1:1 (v/v)). (yield=1.08 g, 56%)

Figure 11:
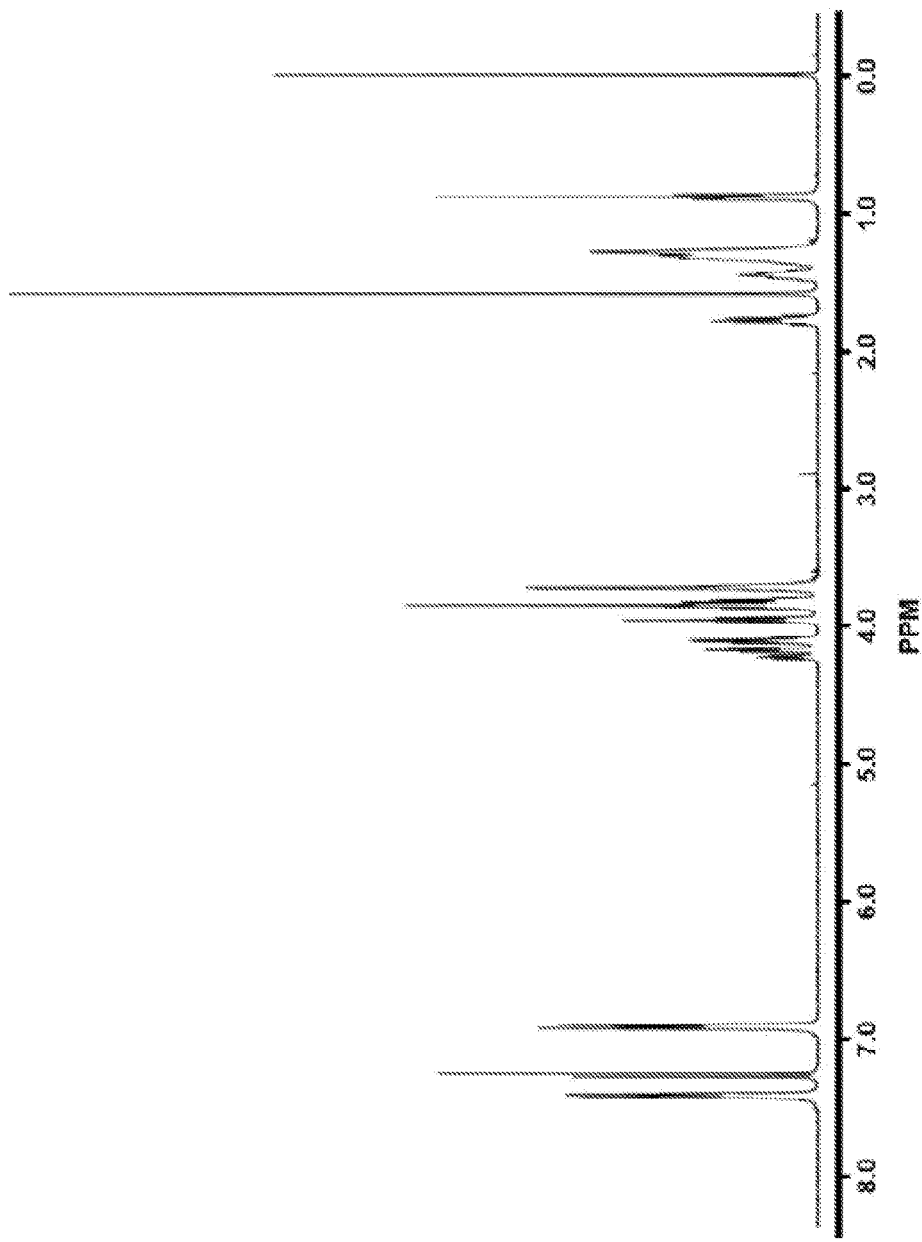
FIG. 11 shows the synthesis of 3,4,5-tris[2-(2-{2-[4-(4'-octyloxy)hydroxybiphenyl]ethoxy}ethoxy)ethoxy]benzoic acid methyl ester.

$^1$H NMR (400 MHz, CDCl$_3$): δ 7.44-7.41 (m, 12H), 7.29 (s, 2H), 6.94-6.90 (m, 12H), 4.25-4.22 (t, 2H), 4.20-4.17 (t, 4H), 4.13-4.09 (m, 6H), 3.98-3.95 (t, 6H), 3.88-3.80 m (m, 12H), 3.86 (s, 3H), 3.73-3.70 (m, 12H), 1.82-1.75 (m, 6H), 1.47-1.28 (m, 30H), 0.90-0.87 (t, 9H). (See, FIG. 11).

Example 2

Synthesis of 3,4,5-tris[2-(2-{2-[4-(4'-octyloxy)hydroxybiphenyl]ethoxy}ethoxy)ethoxy]benzyl alcohol 3,4,5-tris[2-(2-{2-[4-(4'-octyloxy)-hydroxybiphenyl]ethoxy}ethoxy)ethoxy]benzoic acid methyl ester (0.50 g, 0.35 mmol) was dissolved in chloroform (CHCl$_3$, 5 mL) in a 25 mL 1 neck flask and, then, lithium aluminium hydride (0.13 g, 3.51 mmol) was added slowly. The reaction mixture was stirred at room temperature for 2 hr. After reaction, distilled water was added to the mixture in an ice bath. A few drops of sulfuric acid (H$_2$SO$_4$, 2 M) was then added to the mixture for neutralization. 200 mL of distilled water was added to the mixture and extraction was carried out by using 300 mL of chloroform. The solvents were all removed. (yield=0.46 g, 94%)

Figure 12:
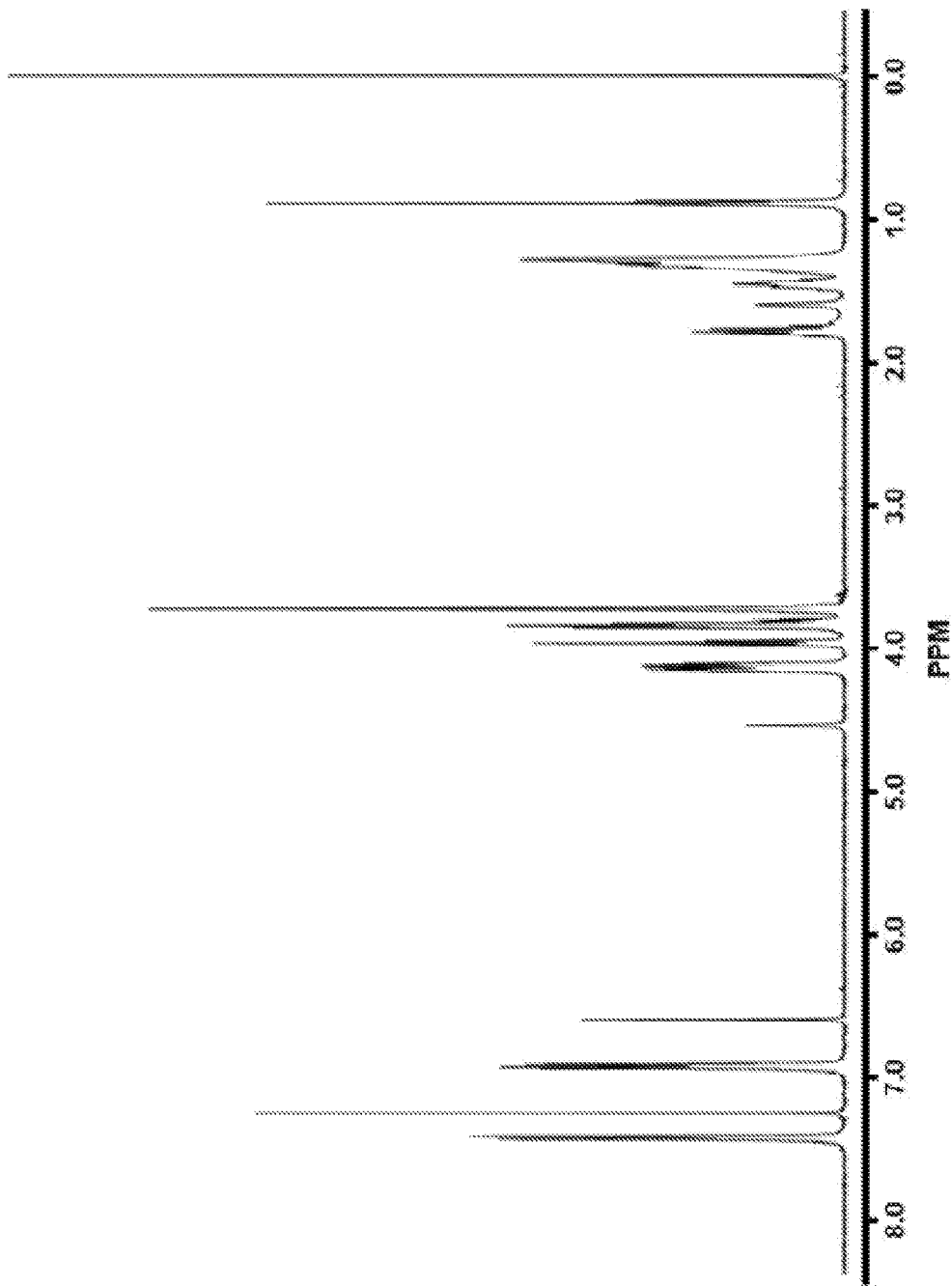
FIG. 12 shows the synthesis of 3,4,5-tris[2-(2-{2-[4-(4'-octyloxy)hydroxybiphenyl]ethoxy}ethoxy)ethoxy]benzyl alcohol.

$^1$H NMR: δ 7.44-7.41 (m, 12H), 6.94-6.90 (m, 12H), 6.60 (s, 2H), 4.53 (s, 2H), 4.17-4.10 (m, 12H), 3.98-3.95 (t, 6H), 3.85-3.79 (m, 12H), 3.73 (s, 12H), 1.82-1.75 (m, 6H), 1.47-1.28 (m, 30H), 0.90-0.87 (t, 9H). (See, FIG. 12).

Example 3

Synthesis of 3,4,5-tris[2-(2-{2-[4-(4'-octyloxy)hydroxybiphenyl]ethoxy}ethoxy)ethoxy]benzyl bromide 3,4,5-tris[2-(2-{2-[4-(4'-octyloxy)-hydroxybiphenyl]ethoxy}ethoxy)ethoxy]benzyl alcohol (0.46 g, 0.33 mmol) and 5 mL of chloroform were added to a 100 mL 1 neck flask. Trimethylsilyl briomide (0.0757 g, 0.495 mmol) was added dropwise to the reaction mixture at 0° C. The thus obtained mixture was stirred at 0° C. for 1 hr and, then, stirred at room temperature for 3 hr. After reaction, all the solvents were removed. (yield: 0.38 g, 79%)

Figure 13:
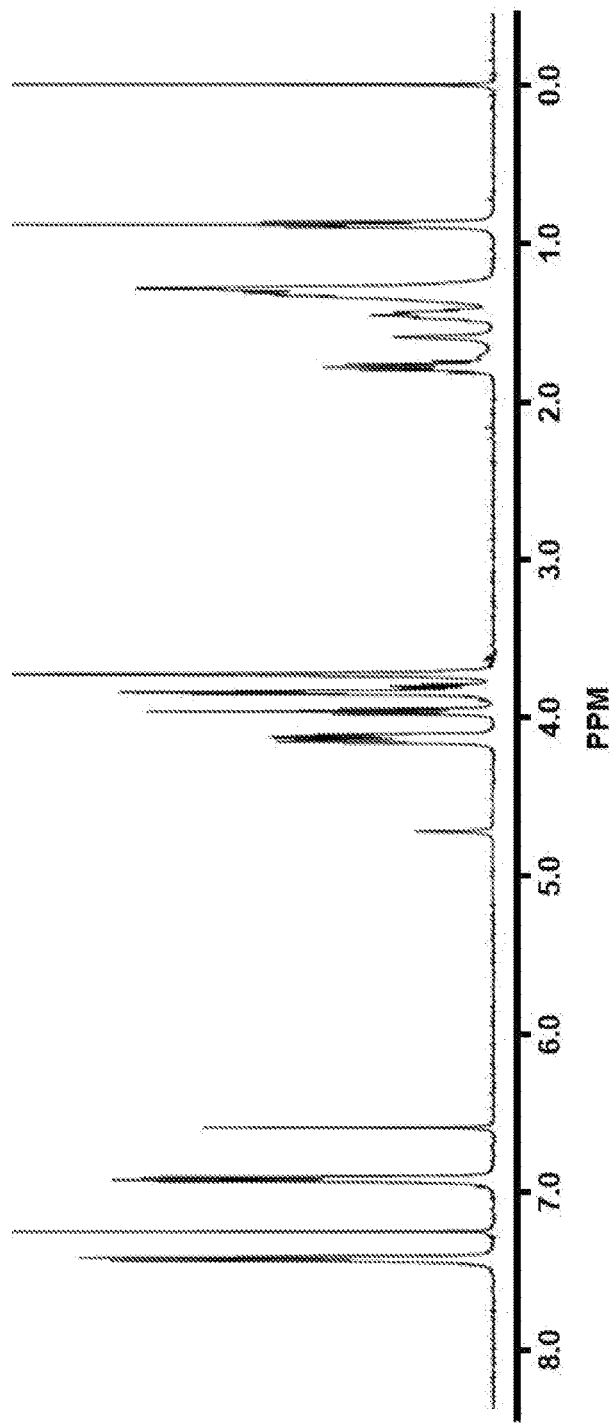
FIG. 13 shows the Synthesis of 3,4,5-tris[2-(2-{2-[4-(4'-octyloxy)hydroxybiphenyl]ethoxy}ethoxy)ethoxy]benzyl bromide.

$^1$H NMR: δ 7.44-7.42 (m, 12H), 6.94-6.90 (m, 12H), 6.66 (s, 2H), 4.36 (s, 2H), 4.14-4.12 (m, 12H), 3.98-3.95 (t, 6H), 3.85-3.80 (m, 12H), 3.73 (s, 12H), 1.82-1.75 (m, 6H), 1.47-1.28 (m, 30H), 0.90-0.87 (t, 9H). (See, FIG. 13).

Example 4

Synthesis of 3,4,5-tris[2-(2-{2-[4-(4'-octyloxy)hydroxybiphenyl]ethoxy}ethoxy)ethoxy]benzyl azide 3,4,5-tris[2-(2-{2-[4-(4'-octyloxy)-hydroxybiphenyl]ethoxy}ethoxy)ethoxy]benzyl bromide (0.3 g 0.206 mmol), 5 mL of DMF and sodium azide (0.26 g, 4.12 mmol) were added to a 25 mL 1 neck flask. The reaction mixture was stirred for one day under argon atmosphere. After reaction, the solvent was removed. Products were separated by column chromatography (silica, chloroform:ethyl acetate=1:1 (v/v)). (yield: 0.16 g, 54%)

Figure 14:
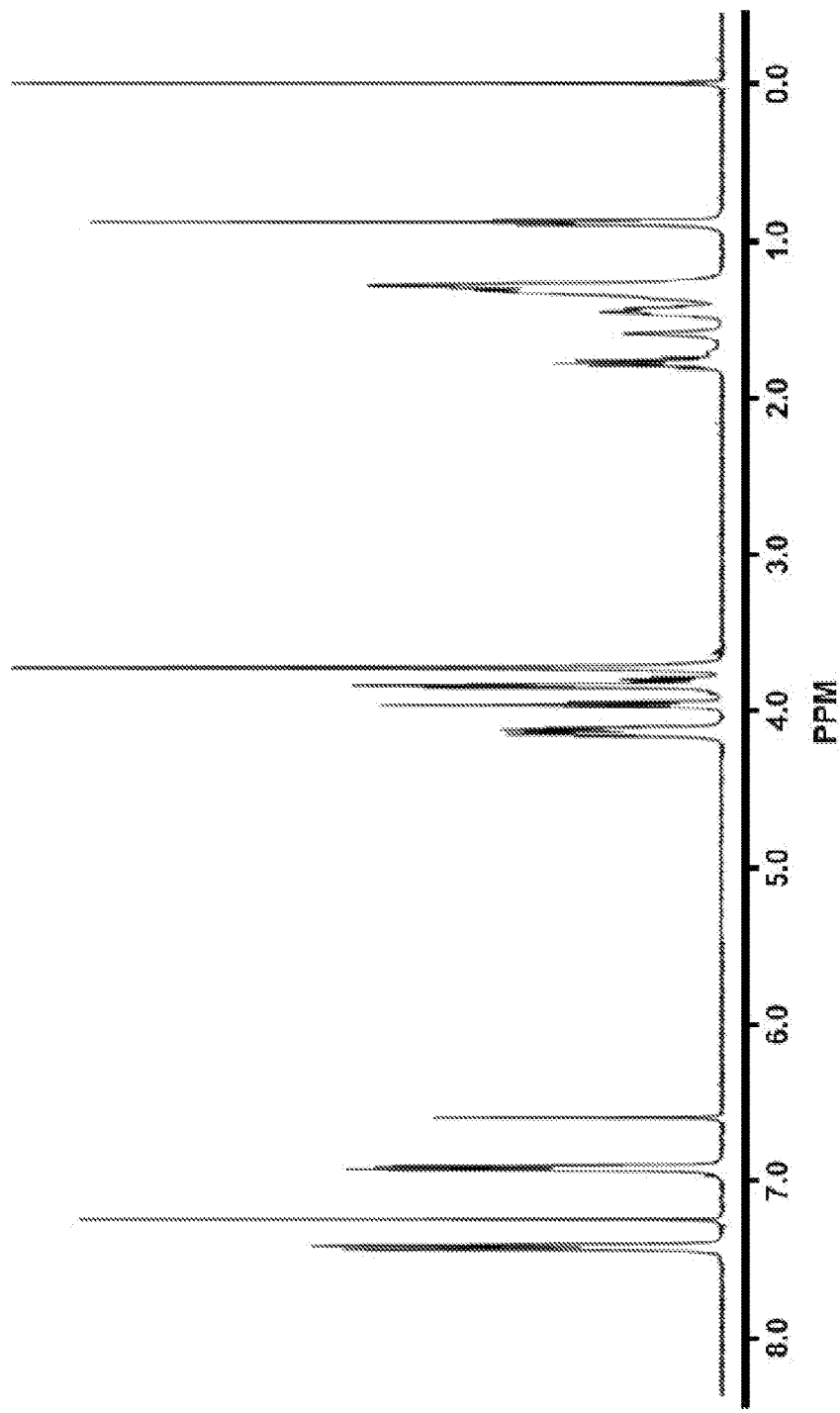
FIG. 14 shows the synthesis of 3,4,5-tris[2-(2-{2-[4-(4'-octyloxy)hydroxybiphenyl]ethoxy}ethoxy)ethoxy]benzyl azide.

$^1$H NMR: δ 7.44-7.41 (m, 12H), 6.94-6.90 (m, 12H), 6.52 (s, 2H), 4.20-4.10 (m, 14H), 3.98-3.95 (t, 6H), 3.86-3.79 (m, 12H), 3.73 (s, 12H), 1.82-1.75 (m, 6H), 1.47-1.28 (m, 30H), 0.90-0.87 (t, 9H). (See, FIG. 14).

Example 5

Synthesis of 3,4,5-tris[2-(2-{2-[4-(4'-octyloxy)hydroxybiphenyl]ethoxy}ethoxy)ethoxy]benzoic acid 3,4,5-tris[2-(2-{2-[4-(4'-octyloxy)-hydroxybiphenyl]ethoxy}ethoxy)ethoxy]benzoic acid methyl ester (1.08 g, 0.76 mmol) and 20 mL of tetrahydrofuran were added to a 100 mL 1 neck flask. Aqueous sodium hydroxide (10 M) and 15 mL of methanol were added thereto. The reaction mixture was stirred at 60° C. for 2.5 hr. After reaction, hydrochloric acid was added. After filtration, the thus obtained products were dissolved in chloroform and, then, precipitated in ethanol. (yield: 0.88 g, 82%)

Figure 15:
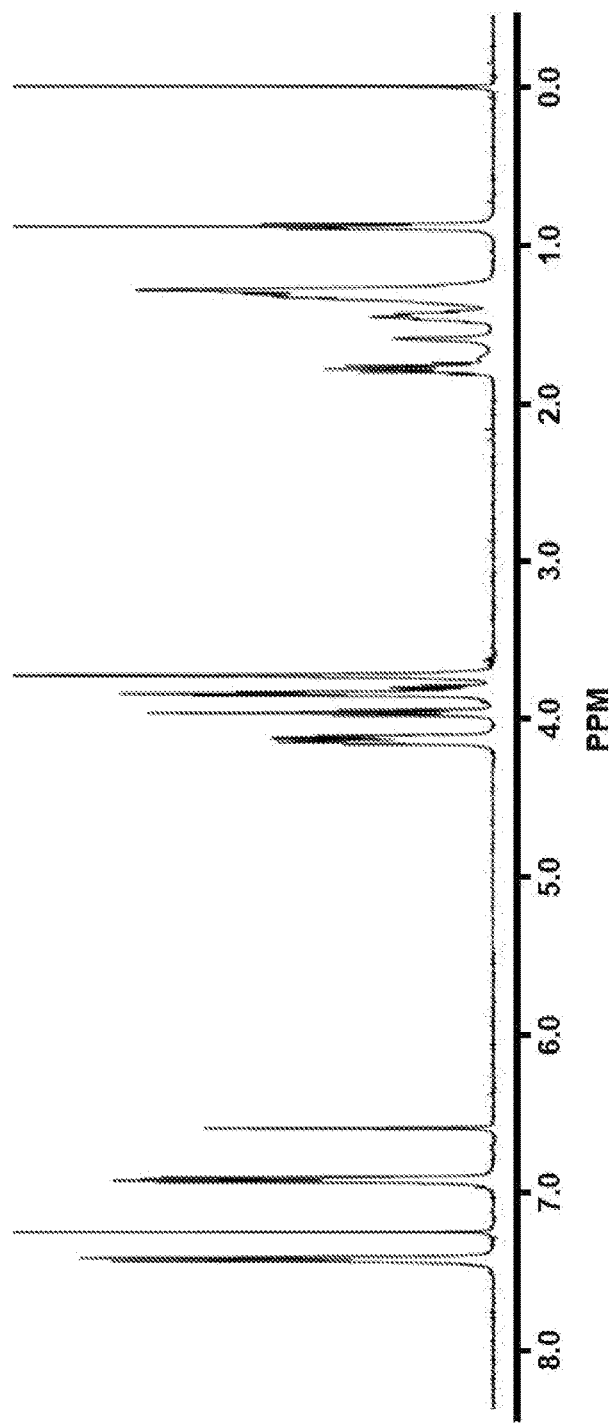
FIG. 15 shows the synthesis of 3,4,5-tris[2-(2-{2-[4-(4'-octyloxy)hydroxybiphenyl]ethoxy}ethoxy)ethoxy]benzoic acid.

$^1$H NMR (400 MHz, CDCl$_3$): δ 7.43-7.41 (m, 12H), 7.33 (s, 2H), 6.93-6.90 (m, 12H), 4.26-4.24 (t, 2H), 4.19-4.17 (t, 4H), 4.13-4.09 (m, 6H), 3.97-3.94 (t, 6H), 3.87-3.83 (m, 12H), 3.73-3.71 (m, 12H), 1.81-1.74 (m, 6H), 1.47-1.28 (m, 30H), 0.90-0.86 (t, 9H). (See, FIG. 15).

Example 6

Synthesis of 3,4,5-tris[2-(2-{2-[4-(4'-octyloxy)hydroxybiphenyl]ethoxy}ethoxy)ethoxy]acyl chloride 3,4,5-tris[2-(2-{2-[4-(4'-octyloxy)-hydroxybiphenyl]ethoxy}ethoxy)ethoxy]benzoic acid (0.88 g, 0.62 mmol) and thionyl chloride (1.85 g, 15.62 mmol) were added to a 100 mL 1 neck flask and, then, the mixture was stirred at 60° C. for 8 hr. The solvent was removed. (yield: 0.88 g, 100%)

Figure 16:
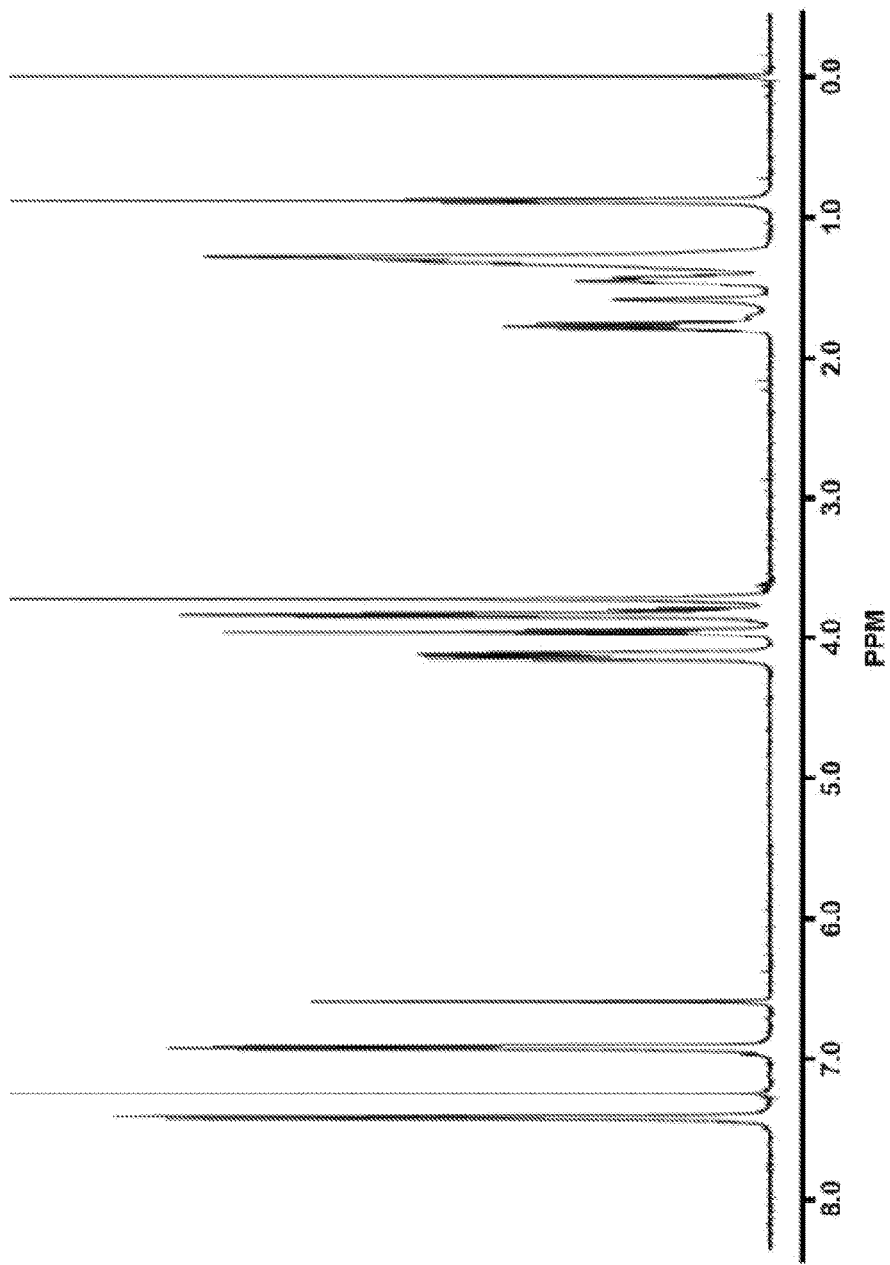
FIG. 16 shows the synthesis of 3,4,5-tris[2-(2-{2-[4-(4'-octyloxy)hydroxybiphenyl]ethoxy}ethoxy)ethoxy]acyl chloride

$^1$H NMR (400 MHz, CDCl$_3$): δ 7.44-7.42 (m, 12H), 7.37 (s, 2H), 6.94-6.91 (m, 12H), 4.30-4.29 (t, 2H), 4.19-4.18 (t, 4H), 4.13-4.09 (m, 6H), 3.97-3.95 (t, 6H), 3.87-3.80 (m, 12H), 3.74-3.69 (m, 12H), 1.81-1.76 (m, 6H), 1.48-1.27 (m, 30H), 0.90-0.87 (t, 9H). (See, FIG. 16).

Example 7

Synthesis of 3,5-[2-(2-{2-[4-(4'-octyloxy)hydroxybiphenyl]ethoxy}ethoxy)ethoxy]benzoic acid methyl ester 2-(2-{2-[4-(4'-octyloxy)-hydroxybiphenyl]ethoxy}ethoxy)ethyl p-toluenesulfonate (6.64 g, 22.25 mmol) was dissolved in purified N,N-dimethylformamide (DMF, 25 mL) in a 250 mL 1 neck round flask and, then, methyl 3,5-hydroxybenzoate (0.96 g, 5.56 mmol) and potassium carbonate (2.31 g, 16.68 mmol) were added. The reaction mixture was refluxed at 80° C. for 2 days under nitrogen atmosphere. After removing the solvent, 200 mL of distilled water and, then, extraction was performed by using 600 mL of chloroform. After removing all the solvents, products were separated by column chromatography (silica, methylene chloride/ethyl acetate=5:1 (v/v)). (yield=1.64 g, 29%)

Figure 17:
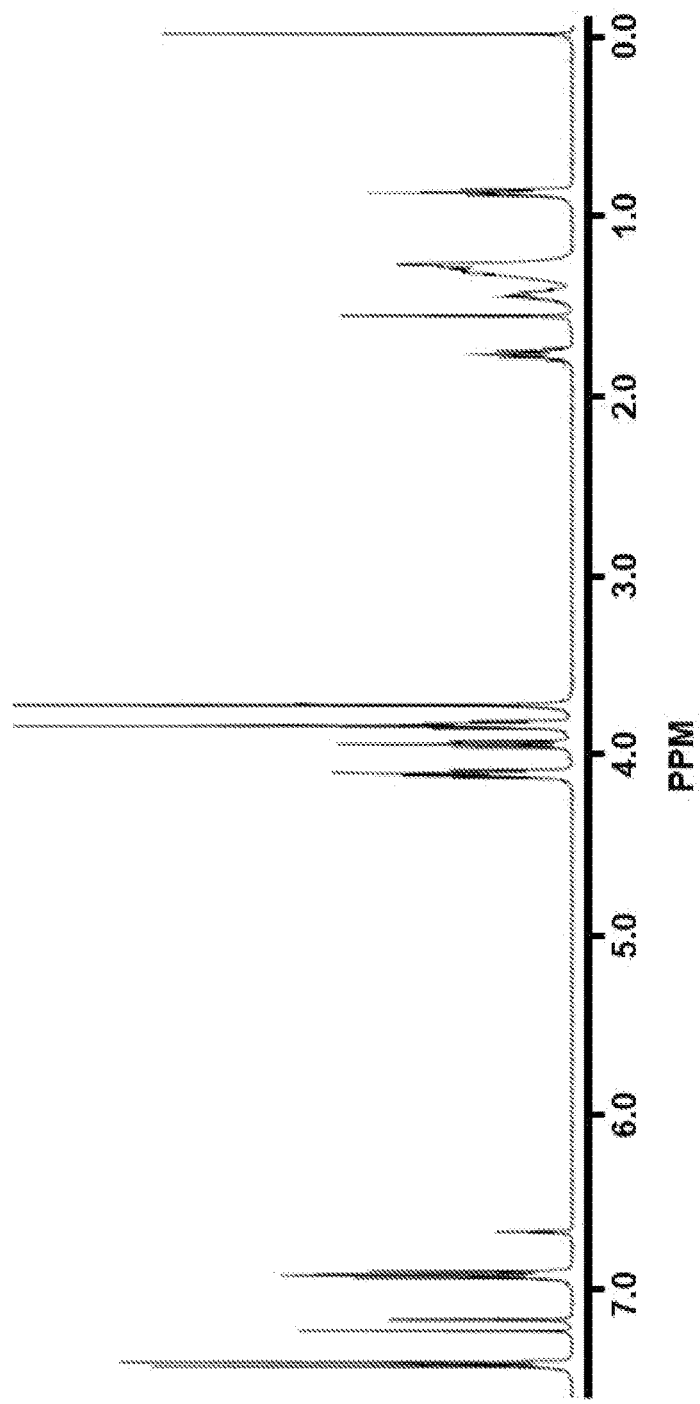
FIG. 17 shows the synthesis of 3,5-[2-(2-{2-[4-(4'-octyloxy)hydroxybiphenyl]ethoxy}ethoxy)ethoxy]benzoic acid methyl ester.

$^1$H NMR (400 MHz, CDCl$_3$): δ 7.45-7.43 (m, 4H), 7.19 (d, 2H), 6.95-6.93 (m, 4H), 6.7 (s, 1H), 4.15-4.13 (m, 4H), 4.00-3.97 (t, 2H), 3.90-3.87 (m, 4H), 3.86 (s, 3H), 3.75 (s, 4H), 1.81-1.77 (m, 2H), 1.50-1.29 (m, 10H), 0.90-0.87 (t, 3H). (See, FIG. 17).

Example 8

Synthesis of 3,5-[2-(2-{2-[4-(4'-octyloxy)hydroxybiphenyl]ethoxy}ethoxy)ethoxy]benzyl alcohol 3,5-[2-(2-{2-[4-(4'-octyloxy)-hydroxybiphenyl]ethoxy}ethoxy)ethoxy]benzoic acid methyl ester (1.64 g, 1.61 mmol) was dissolved in chloroform (CHCl$_3$, 20 mL) in a 100 mL 1 neck flask and, then, lithium aluminium hydride (0.61 g, 16.06 mmol) was added slowly. The reaction mixture was agitated at room temperature for 2 hr. A few drops of sulfuric acid (H$_2$SO$_4$, 2 M) were added to the mixture for neutralization (pH 7). 200 mL of distilled water was added to the mixture and extraction was carried out by using 600 mL of chloroform. All the solvents were removed. (yield=1.4 g, 88%)

Figure 18:
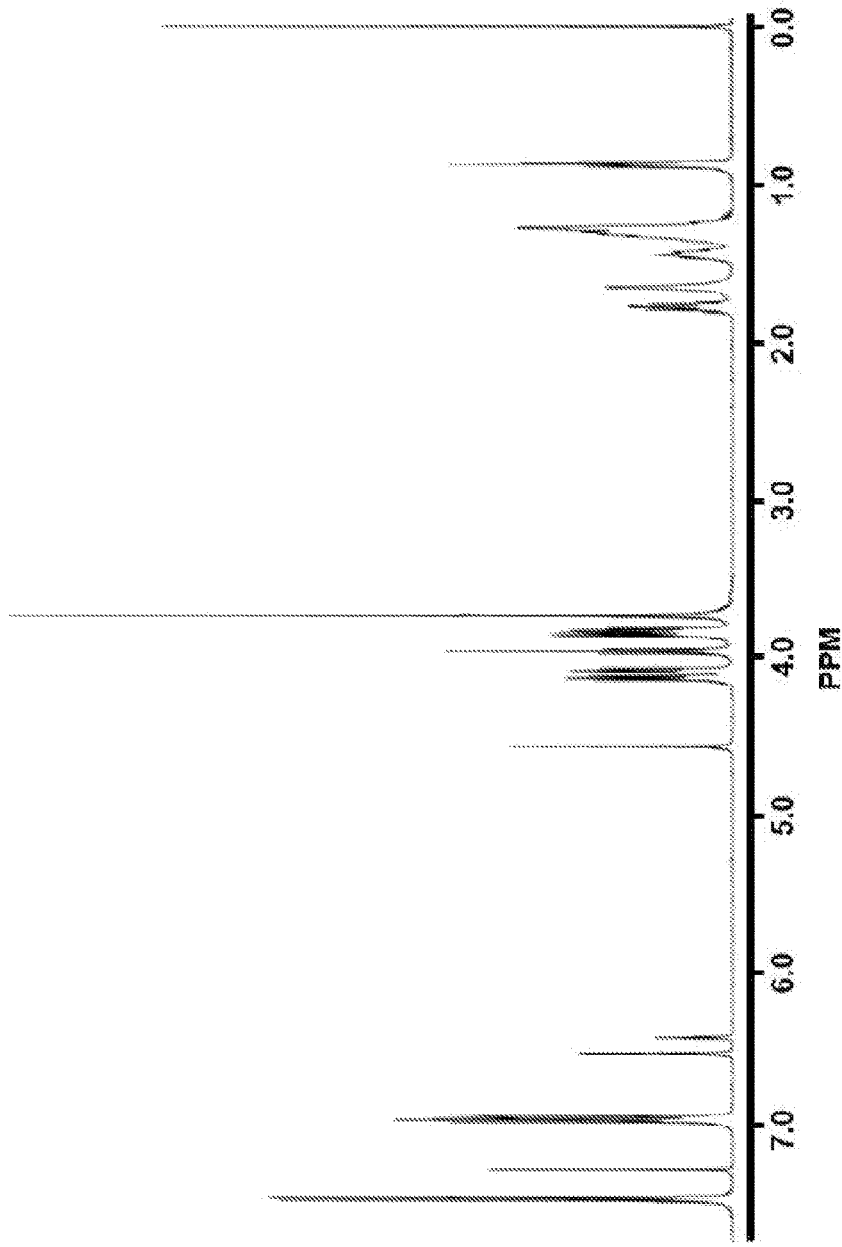
FIG. 18 shows the synthesis of 3,5-[2-(2-{2-[4-(4'-octyloxy)hydroxybiphenyl]ethoxy}ethoxy)ethoxy]benzyl alcohol.

$^1$H NMR: δ 7.45-7.43 (m, 4H), 6.96-6.93 (m, 4H), 6.52-6.51 (d, 2H), 6.42 (s, 1H), 4.57 (s, 2H), 4.14-4.10 (m, 4H), 3.99-3.96 (t, 2H), 3.87-3.84 (m, 4H), 3.74 (s, 4H), 1.81-1.77 (m, 2H), 1.46-1.29 (m, 10H), 0.90-0.87 (t, 3H). (See, FIG. 18).

Example 9

Synthesis of 4-[2-(2-{2-[4-(4'-octyloxy)hydroxybiphenyl]ethoxy}ethoxy)ethoxy]benzoic acid methyl ester 2-(2-{2-[4-(4'-octyloxy)-hydroxybiphenyl]ethoxy}ethoxy)ethyl p-toluenesulfonate (2.3 g, 3.93 mmol) was dissolved in purified N,N-dimethylformamide (DMF, 25 mL) in a 250 mL 1 neck round flask and, then, methyl 4-hydroxybenzoate (0.39 g, 2.62 mmol) and potassium carbonate (0.54 g, 3.93 mmol) were added. The reaction mixture was refluxed at 80° C. for one day under nitrogen atmosphere. After removing the solvent, 200 mL of distilled water was added and, then, extraction was performed by using 600 mL of chloroform. After removing all the solvents, products were separated by column chromatography (silica, methylene chloride/ethyl acetate=12:1 (v/v)). (yield=0.8 g, 54%,)

Figure 19:
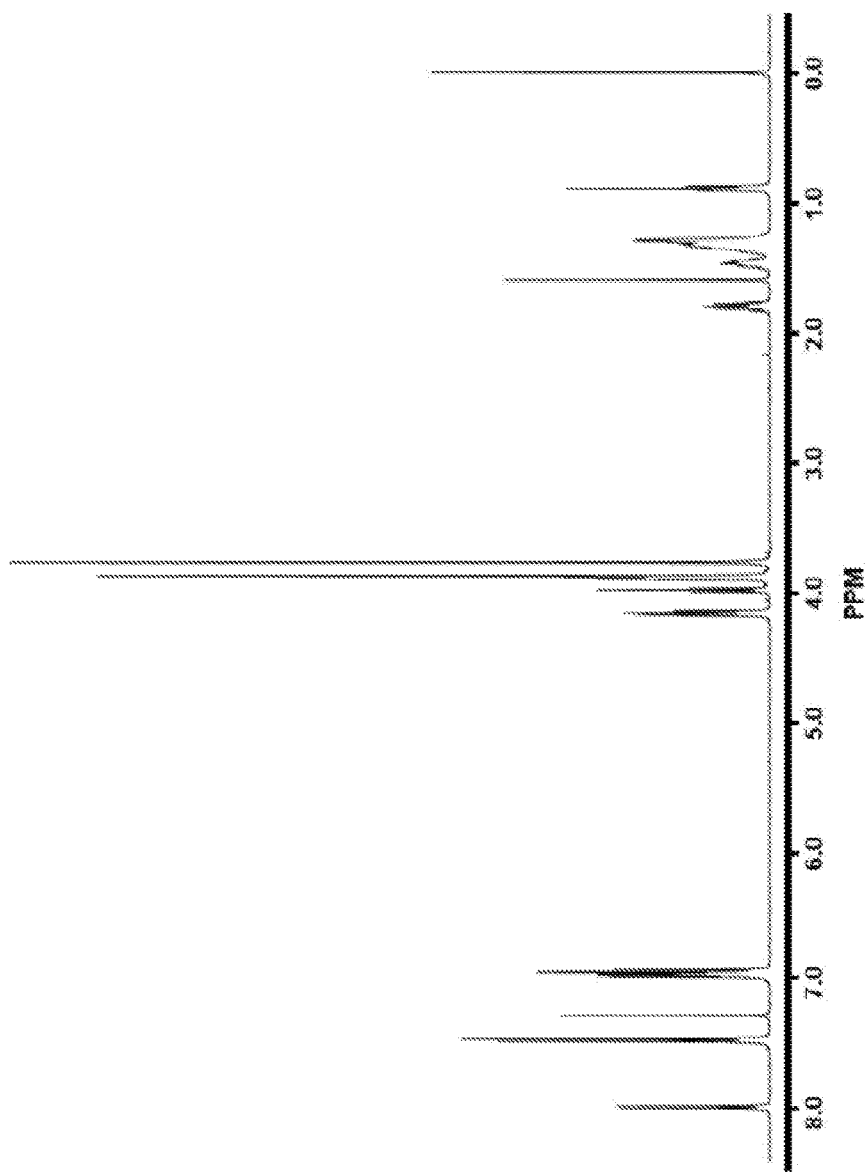
FIG. 19 shows the synthesis of 4-[2-(2-{2-[4-(4'-octyloxy)hydroxybiphenyl]ethoxy}ethoxy)ethoxy]benzoic acid methyl ester.

$^1$H NMR (400 MHz, CDCl$_3$): δ 7.97-7.95 (d, 2H), 7.46-7.44 (d, 4H), 6.96-6.90 (m, 6H), 4.18-4.14 (m, 4H), 3.99-3.96 (t, 2H), 3.90-3.87 (m, 4H), 3.87 (s, 3H), 3.76 (s, 4H), 1.83-1.76 (m, 2H), 1.84-1.29 (m, 10H), 0.90-0.87 (t, 3H). (See, FIG. 19).

Example 10

Synthesis of 4-[2-(2-{2-[4-(4'-octyloxy)hydroxybiphenyl]ethoxy}ethoxy)ethoxy]benzyl alcohol 4-[2-(2-{2-[4-(4'-octyloxy)-hydroxybiphenyl]ethoxy}ethoxy)ethoxy]benzoic acid methyl ester (0.56 g, 0.99 mmol) was dissolved in chloroform (CHCl$_3$, 5 mL) in a 100 mL 1 neck flask and, then, lithium aluminium hydride (0.37 g, 9.91 mmol) was added slowly. The reaction mixture was stirred at room temperature for 2 hr and, after reaction, was dipped in an ice bath. A few drops of sulfuric acid (H$_2$SO$_4$, 2 M) were added to the mixture for neutralization (pH 7). 200 mL of distilled water was added and extraction was carried out by using 600 mL of chloroform. All the solvents were removed. (yield=0.47 g, 88%)

Figure 20:
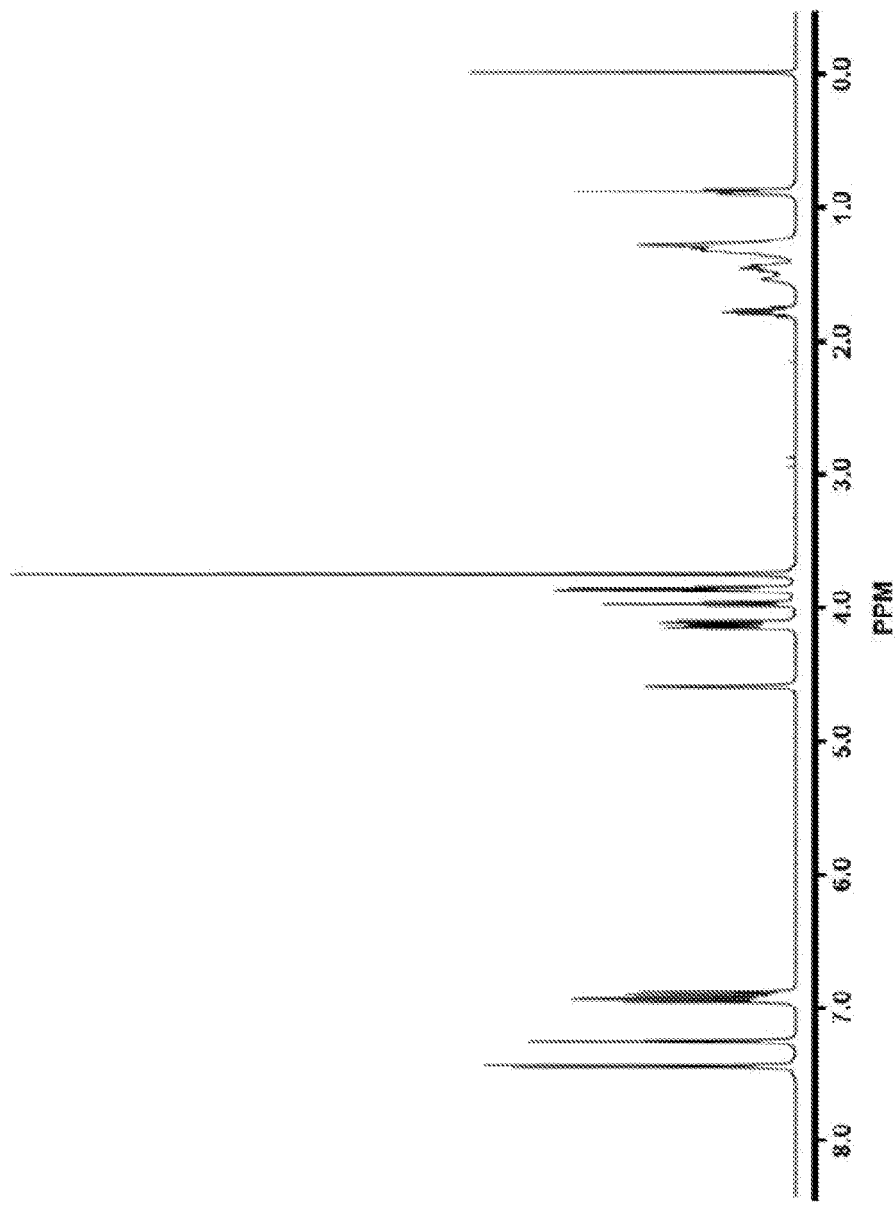
FIG. 20 shows the synthesis of 4-[2-(2-{2-[4-(4'-octyloxy)hydroxybiphenyl]ethoxy}ethoxy)ethoxy]benzyl alcohol.

$^1$H NMR: δ 7.45-7.43 (d, 4H), 7.27-7.24 (d, 2H), 6.96-6.88 (m, 6H), 4.59 (s, 2H), 4.16-4.11 (m, 4H), 3.99-3.96 (t, 2H), 3.89-3.86 (m, 4H), 3.76 (s, 4H), 1.83-1.75 (m, 2H), 1.55-1.29 (m, 10H), 0.90-0.87 (t, 3H). (See, FIG. 20).

Example 11

Synthesis of 3,4,5-tris[2-(2-{2-[4-(4'-octyloxy)hydroxybiphenyl]ethoxy}ethoxy)ethoxy]benzyl methoxy-POSS 3,4,5-[2-(2-{2-[4-(4'-octyloxy)hydroxybiphenyl]ethoxy}ethoxy)ethoxy]benzyl alcohol (0.5 g, 0.358 mmol) and POSS-Isocyanate (0.498 g, 0.430 mmol) were dissolved in tetrahydrofuran (THF, 10 mL) in a 100 mL 1 neck flask and, then, dibutyl tin dilaurate (0.022 g, 0.036 mmol) was added. The reaction mixture was refluxed at 65° C. for 18 hr under nitrogen atmosphere. After reaction, all the solvents were removed and, then, products were separated by column chromatography (silica, chloroform/ethyl acetate=3:1 (v/v)). (yield=0.49 g, 54%)

Figure 21:
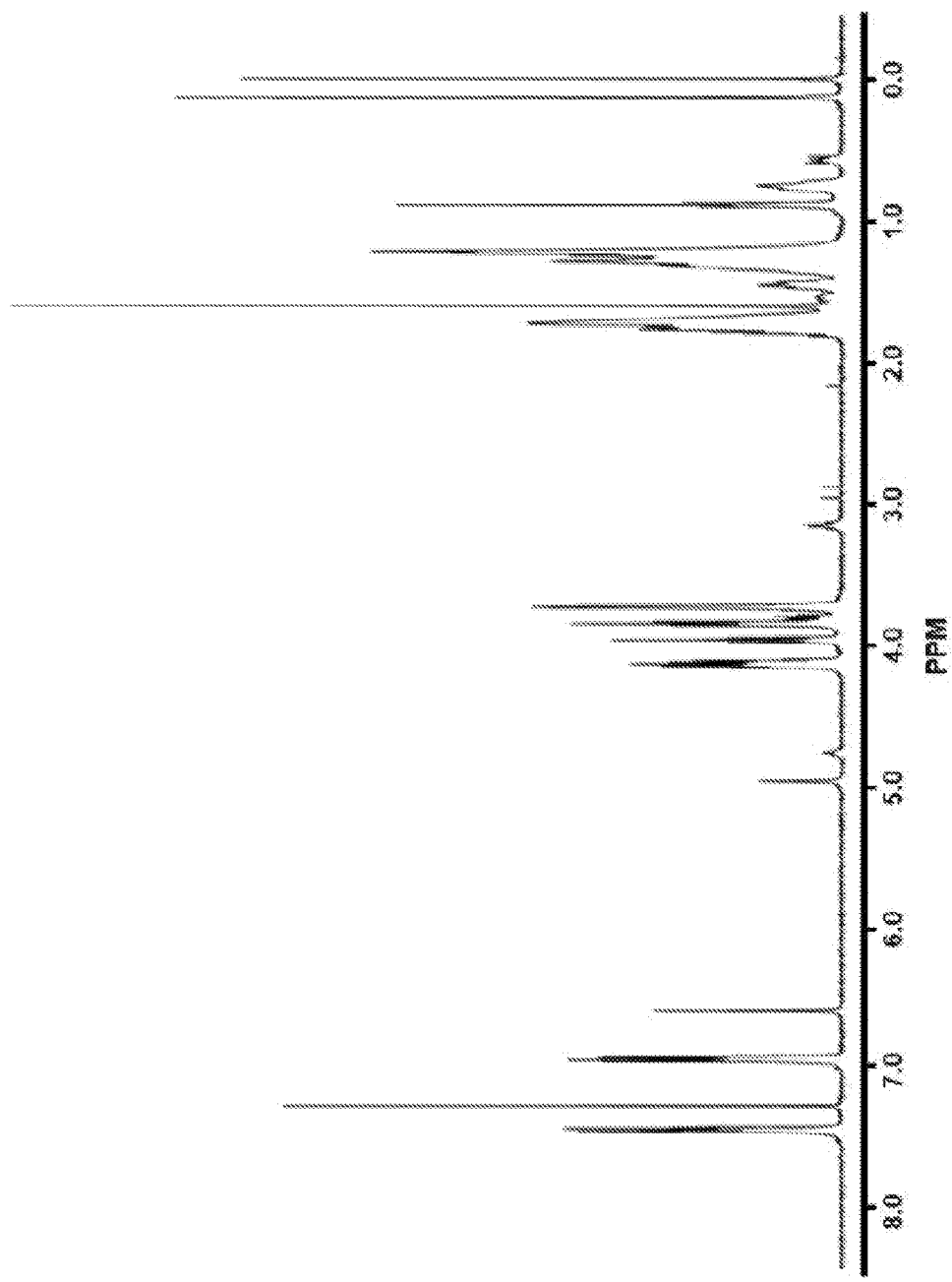
FIG. 21 shows the synthesis of 3,4,5-tris[2-(2-{2-[4-(4'-octyloxy)hydroxybiphenyl]ethoxy}ethoxy)ethoxy]benzyl methoxy-POSS.

$^1$H NMR: 7.44-7.41 (m, 12H), 6.94-6.90 (m, 12H), 6.58 (s, 2H), 4.95 (s, 2H), 4.78-4.75 (t, 1H), 4.16-4.10 (m, 12H), 3.98-3.95 (t, 6H), 3.86-3.79 (m, 12H), 3.77-3.71 (m, 12H), 3.19-3.14 (m, 2H), 1.82-1.65 (m, 48H), 1.57-1.16 (m, 60H), 0.90-0.87 (t, 9H), 0.77-0.72 (m, 7H), 0.59-0.55 (m, 2H), 0.12 (s, 6H). (See, FIG. 21).

Example 12

Synthesis of 3,5-tris[2-(2-{2-[4-(4'-octyloxy)hydroxybiphenyl]ethoxy}ethoxy)ethoxy]benzyl methoxy-POSS 3,5-[2-(2-{2-[4-(4'-octyloxy)hydroxybiphenyl]ethoxy}ethoxy)ethoxy]benzyl alcohol (0.7 g, 0.704 mmol) and POSS-Isocyanate (0.978 g, 0.845 mmol) were dissolved in tetrahydrofuran (THF, 15 mL) in a 100 mL 1 neck flask and, then, dibutyl tin dilaurate (0.054 g, 0.070 mmol) was added. The reaction mixture was refluxed at 65° C. for 18 hr under nitrogen atmosphere. After reaction, the solvent was removed and products were separated by column chromatography (silica, hexane/ethyl acetate=1.5:1 (v/v)). (yield=0.3 g, 20%)

Figure 22:
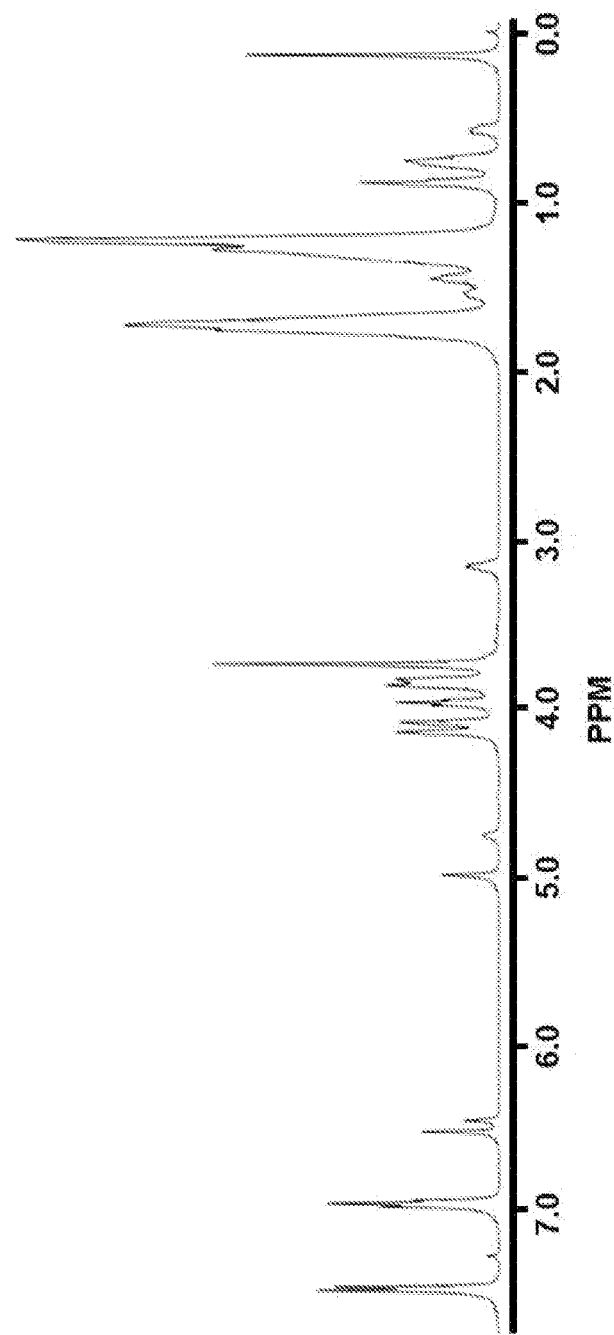
FIG. 22 shows the synthesis of 3,5-tris[2-(2-{2-[4-(4'-octyloxy)hydroxybiphenyl]ethoxy}ethoxy)ethoxy]benzyl methoxy-POSS.

$^1$H NMR: 7.45-7.43 (m, 8H), 6.96-6.93 (m, 8H), 6.51-6.50 (d, 2H), 6.44 (s, 1H), 4.99 (s, 2H), 4.78-4.72 (t, 1H), 4.15-4.09 (m, 8H), 3.99-3.96 (t, 4H), 3.88-3.82 (m, 8H), 3.74 (s, 8H), 3.17-3.15 (m, 2H), 1.84-1.63 (m, 40H), 1.51-1.16 (m, 58H), 0.90-0.87 (t, 6H), 0.81-0.70 (m, 7H), 0.59-0.53 (m, 2H), 0.13 (s, 6H). (See, FIG. 22).

Example 13

Synthesis of 4-[2-(2-{2-[4-(4'-octyloxy)hydroxybiphenyl]ethoxy}ethoxy)ethoxy]benzyl methoxy-POSS 4-[2-(2-{2-[4-(4'-octyloxy)hydroxybiphenyl]ethoxy}ethoxy)ethoxy]benzyl alcohol (0.077 g, 0.144 mmol) and POSS-Isocyanate (0.2 g, 0.173 mmol) were dissolved in tetrahydrofuran (THF, 5 mL) and, then, dibutyl tin dilaurate (0.027 g, 0.043 mmol) was added. The reaction mixture was refluxed at 60° C. for 18 hr under nitrogen atmosphere. After reaction, the solvent was removed and, then, products were separated by column chromatography (silica, hexane/ethyl acetate=2:1 (v/v)). (yield=0.18 g, 76%)

Figure 23:
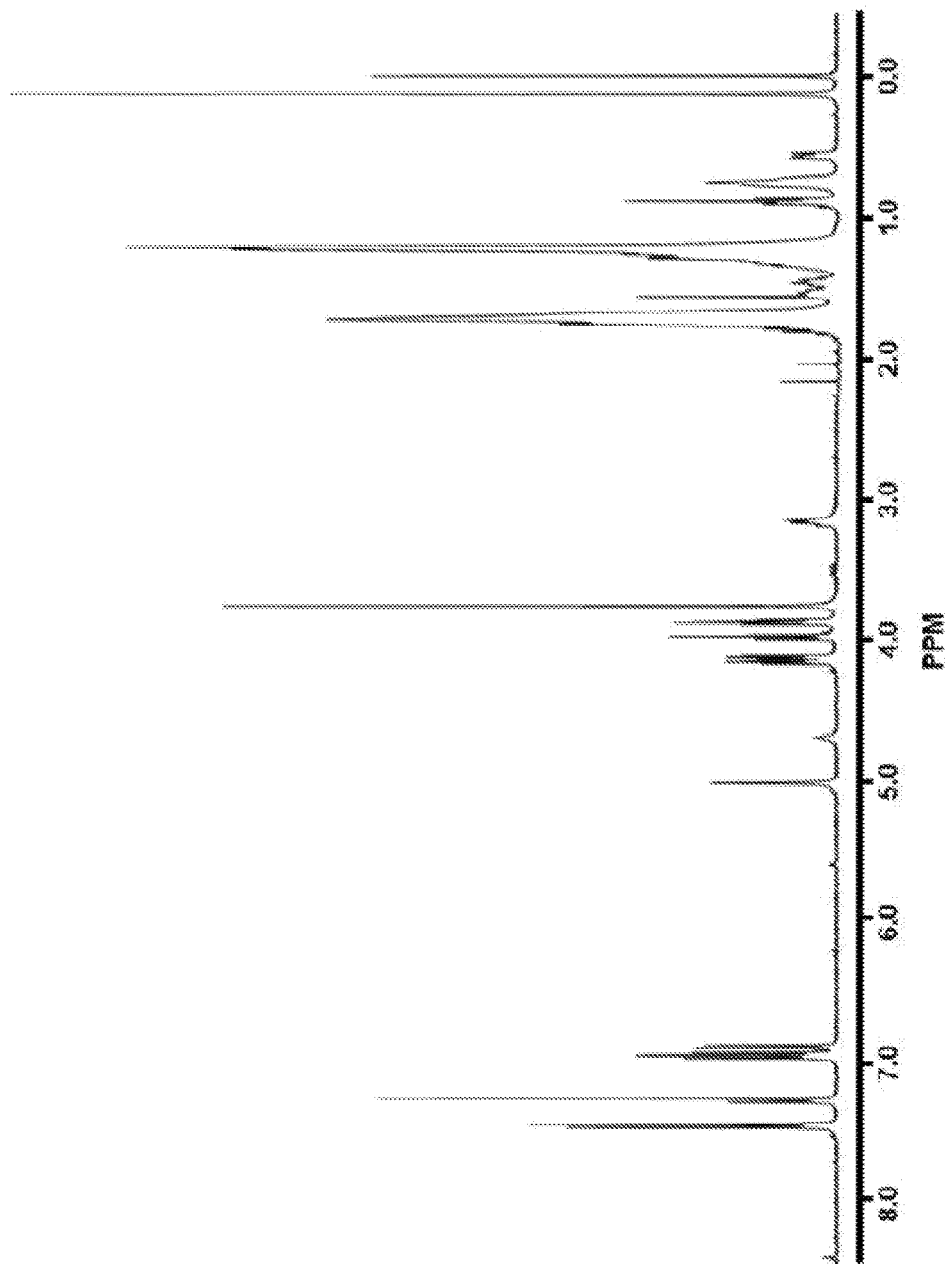
FIG. 23 shows the synthesis of 4-[2-(2-{2-[4-(4'-octyloxy)hydroxybiphenyl]ethoxy}ethoxy)ethoxy]benzyl methoxy-POSS.

$^1$H NMR: 7.45-7.43 (d, 4H), 7.27-7.25 (d, 2H), 6.96-6.92 (t, 4H), 6.89-6.87 (d, 2H), 5.01 (s, 2H), 4.70 (s, 1H), 4.16-4.10 (m, 4H), 3.99-3.96 (t, 2H), 3.88-3.86 (m, 4H), 3.75 (s, 4H), 3.17-3.13 (m, 2H), 1.82-1.72 (m, 44H), 1.56-1.22 (m, 40H), 0.90-0.87 (t, 3H), 0.77-0.73 (m, 7H), 0.58-0.54 (m, 2H), 0.12 (s, 6H). (See, FIG. 23).

The invention claimed is:

1. A liquid crystal compound of the formula 1 which has POSS-dendron structure:

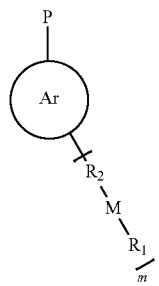

[formula 1]

where Ar is $C_6$-$C_{20}$ aryl,
P is polysilsesquioxane,
Ar and P are linked with oxygen or NCO group,
$R_1$ and $R_2$ are independently $C_1$-$C_{30}$ hydrocarbon,
M is mesogen of compound of the formula 6, and
m is 1-3

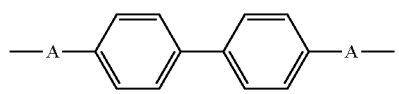

[formula 6]

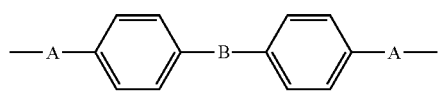

where A is —O—, —COO—, —OCO— or —NHCO—;
B is S, O, $N_2$ or $(CH_2)_n$; and n is 1-20.

2. The liquid crystal compound of claim 1, wherein the polysilsesquioxane is a POSS-dendron-structured liquid crystal compound of formula 2:

$[R-SiO_{1.5}]_n$ [formula 2]

where R is selected from the group consisting of $C_1$-$C_3$ alkyl, $C_1$-$C_3$ alkenyl, $C_3$-$C_{10}$ cycloalkyl, $C_6$-$C_{15}$ aryl, hydrogen and hydroxyl; and n is an integer of 3-1,000.

3. The liquid crystal compound of claim 1, wherein $R_1$ and $R_2$ are independently $C_2$-$C_{30}$ linear or branched alkyl, or $C_2$-$C_{30}$ alkenyl.

4. The liquid crystal compound of claim 1, wherein $R_1$ and $R_2$ are independently $C_1$-$C_{30}$ alkylene, $C_1$-$C_{30}$ alkoxy, $C_1$-$C_{30}$ fluoroalkylene, $C_1$-$C_{30}$ ether, $C_1$-$C_{30}$ fluoroether, or —$OR_3O$—, where $R_3$ is $C_1$-$C_{30}$ alkylene or $C_1$-$C_{30}$ fluoroalkylene.

5. The liquid crystal compound of claim 1, wherein the compound of formula 1 is selected from the compounds of the following formula 5:

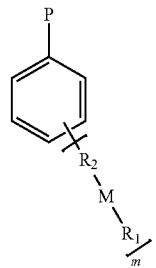

[formula 5]

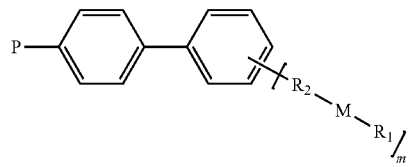

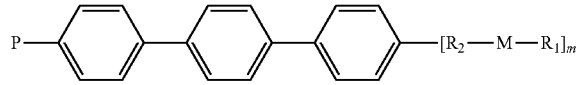

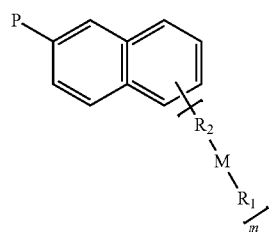

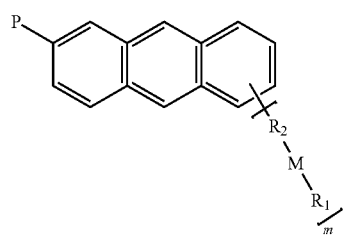

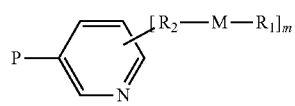

where P is polysilsesquioxane, $R_1$ and $R_2$ are independently $C_1$-$C_{20}$ hydrocarbon, M is mesogen, and m is 1-3.

6. The liquid crystal compound of claim 1, wherein the liquid crystal compound of the POSS-dendron structure has a chemical structure of formula 7

15
16
-continued
[formula 7]
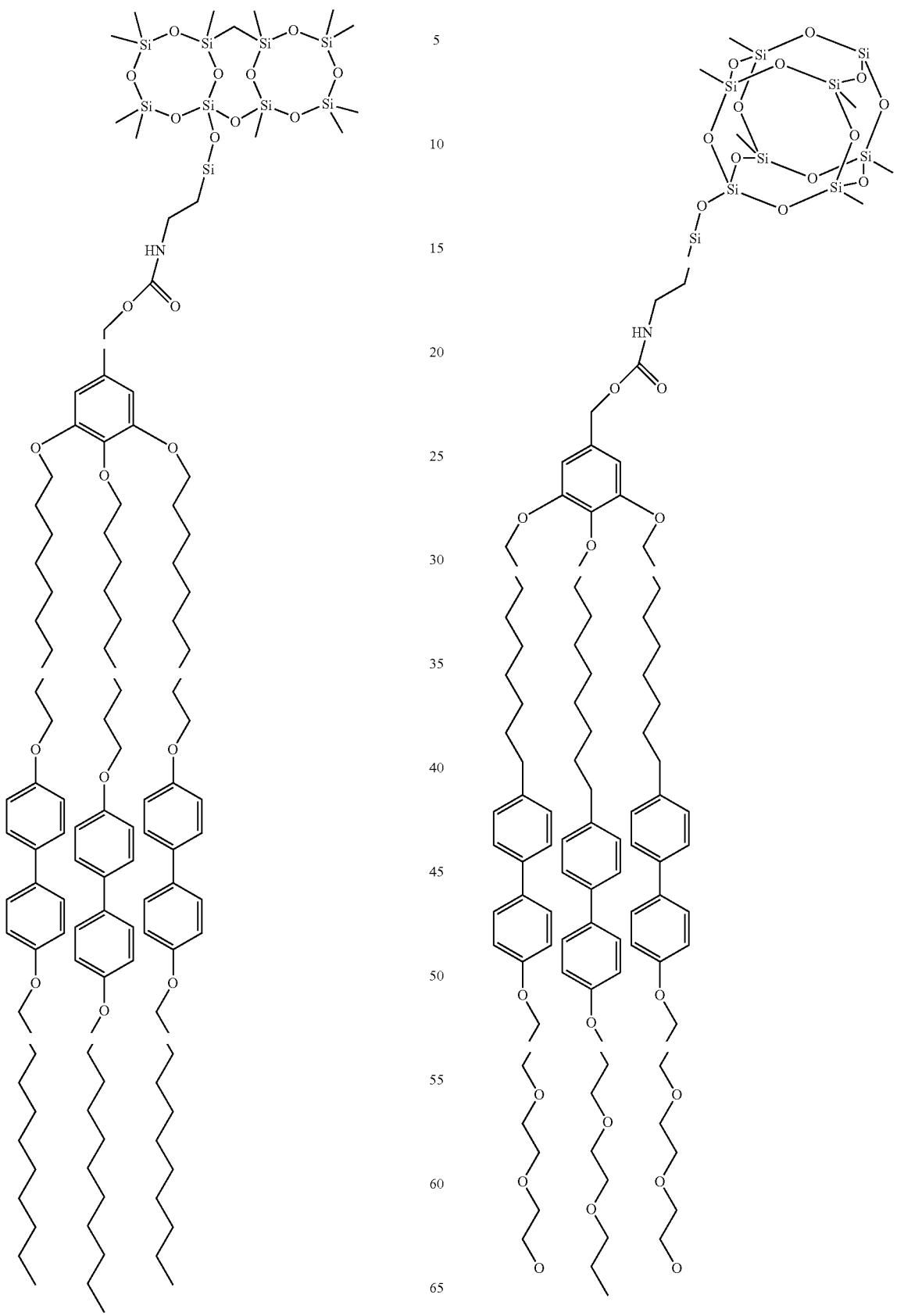

17
-continued
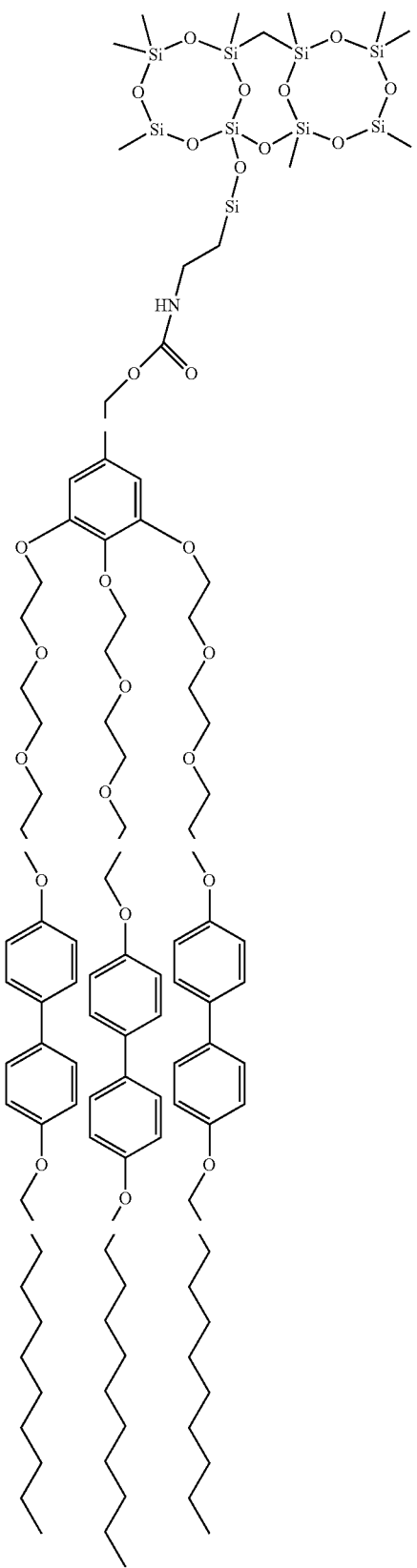
18
-continued
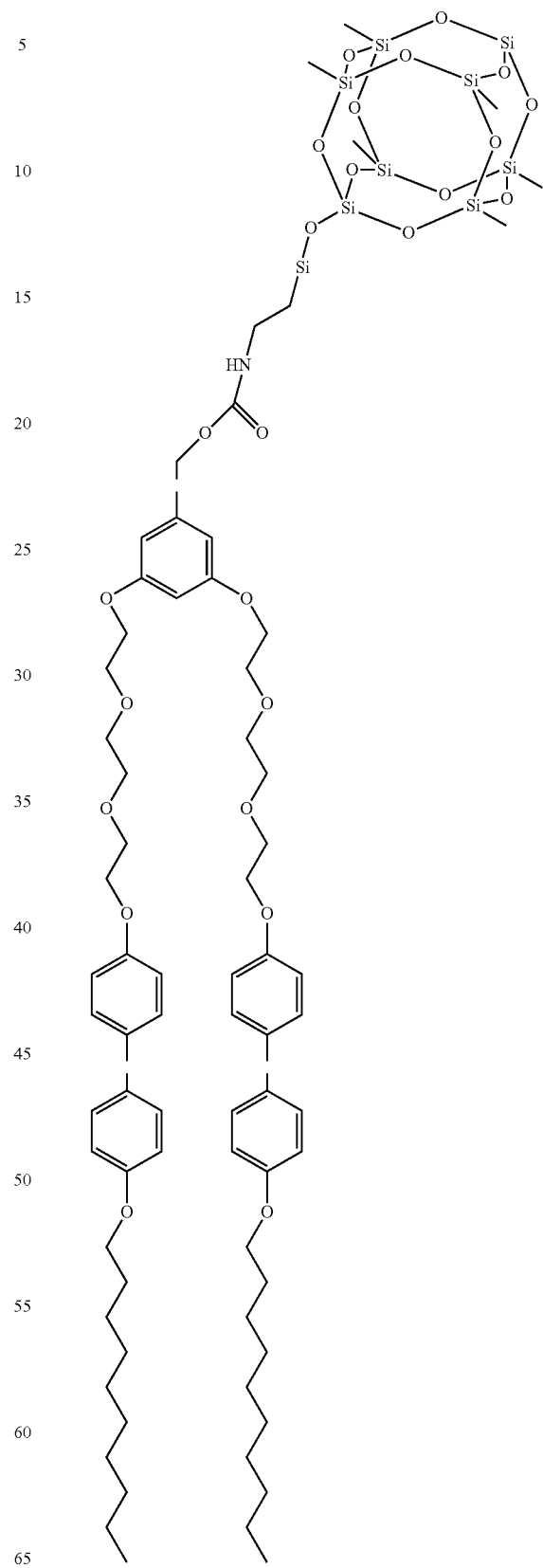

19
-continued
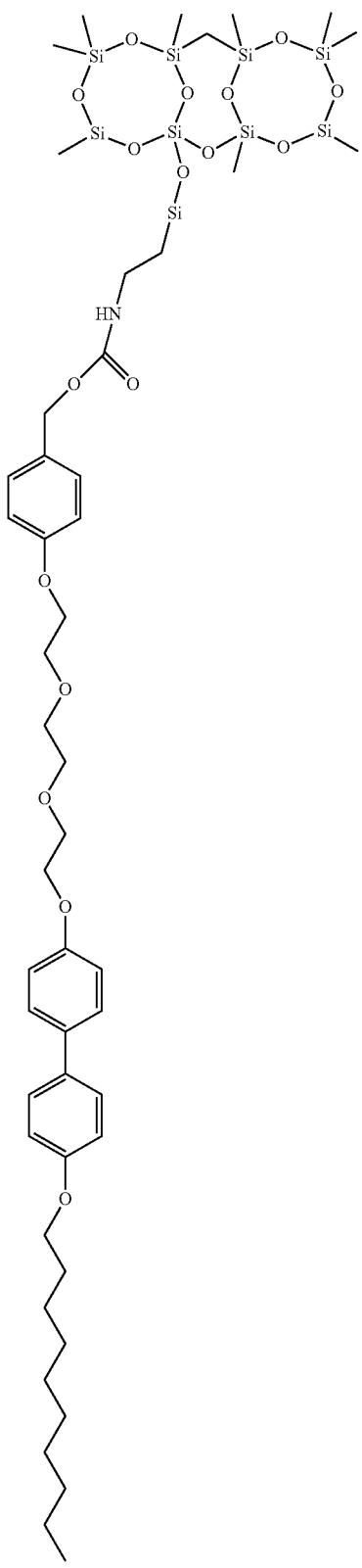
20
-continued
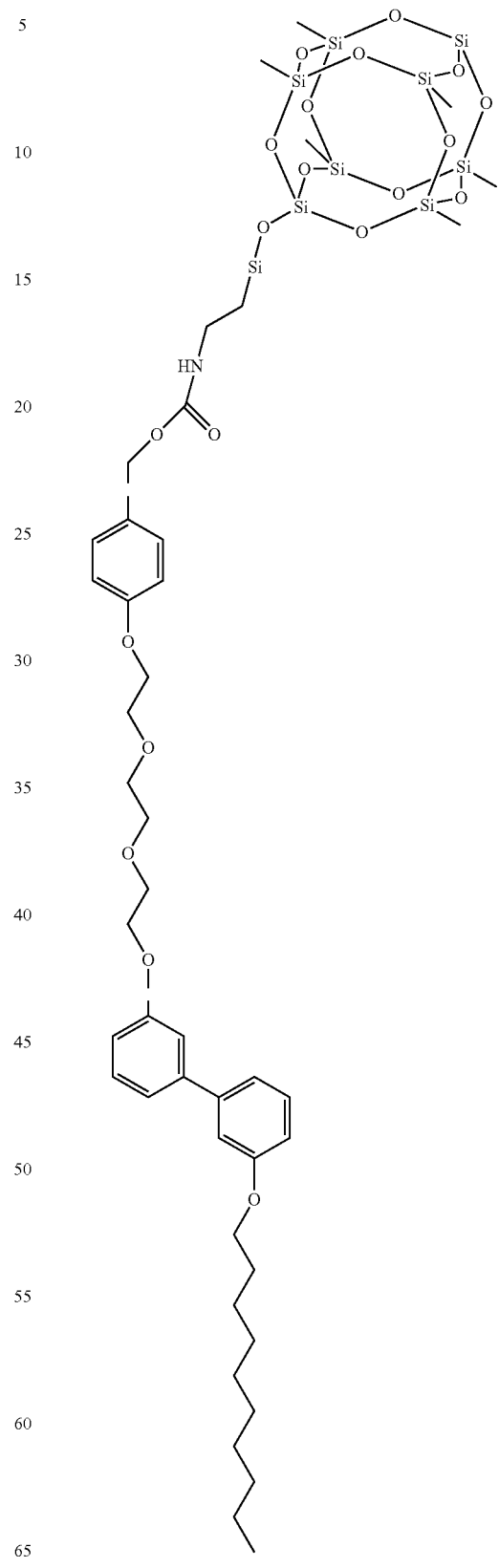

-continued

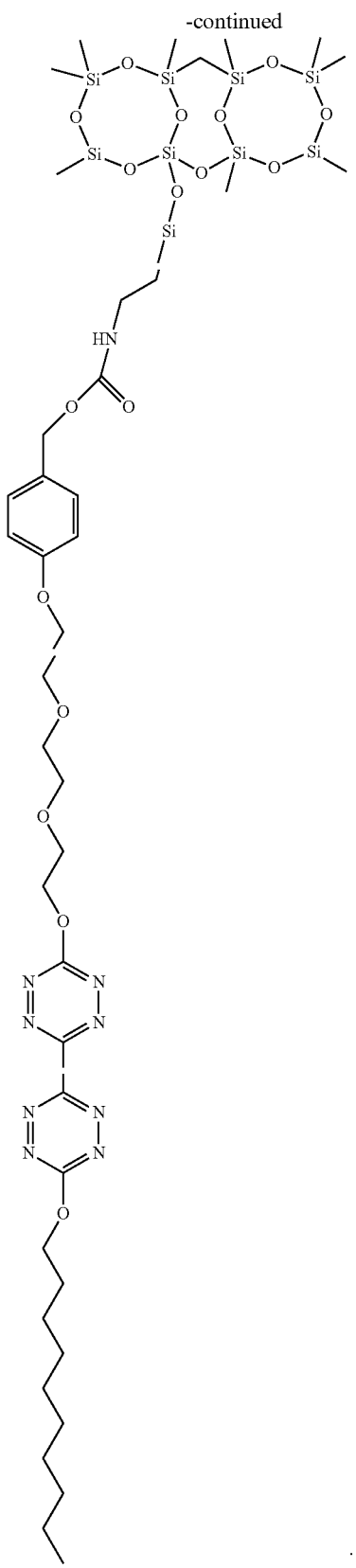

7. The liquid crystal compound of claim 1, wherein the liquid crystal compound of the POSS-dendron structure has a weight average molecular weight of 500-3,000 g/mol.

8. A method for preparing a liquid crystal compound of the following formula 9 which has POSS-dendron structure, comprising:
(i) reacting alkyl chain ($R_1$) with mesogen (M) in a weight ratio of 1:0.8-1.5;
(ii) reacting the $R_1$-M obtained in the step (i) with $R_2$ in a weight ratio of 1:2-4;
(iii) reacting the $R_1$-M-$R_2$ obtained in the step (ii) with benzoate in a certain weight ratio to form $R_1$-M-$R_2$—Ar; and
(iv) reacting the $R_1$-M-$R_2$—Ar with polysilsesquioxane,

[formula 9]

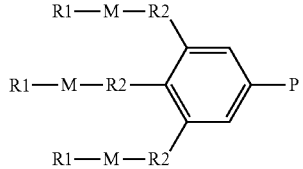

where M is mesogen of compound of the formula 6,

[formula 6]

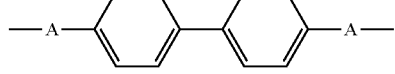

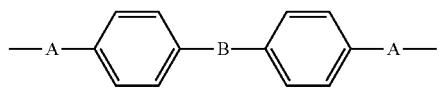

$R_1$ is $CF_3(CF_2)nCH_2CH_2OH$, $CH_3(CH_2)_nBr$, $CH_3(CH_2)_nOH$, $CH_3(OCH_2CH_2)_nOH$, $CH_3(OCH_2CH_2)_nBr$, $CF_3(CF_2)_nBr$, $CF_3(CF_2)_nI$, $CF_3(CF_2)_nCH_2I$, $CF_3(CF_2)_nCH_2OH$, $CF_3(CF_2)_nCH_2CH_2I$ or $CH_3(CH_2)_nCl$;

$R_2$ is $Cl(CH_2)_nCl$, $Br(CH_2)_nBr$, $HO(CH_2)_nOH$, $ClCH_2(CH_2OCH_2)_nCH_2Cl$, $Cl(CF_2)_nCl$, $I(CF_2)_nI$, $Br(CF_2)_nBr$, $HOCH_2(CH_2OCH_2)_nCH_2OH$, or $HOCH_2(CF_2)_nCH_2OH$;

Ar is benzene; and

P is polysilsesquioxane.

9. The method of claim 8, wherein the $R_1$-M-$R_2$—Ar is reacted with the polysilsesquioxane after introducing —NCO to the end group of the polysilsesquioxane at the step (iv).

10. A method for forming a liquid crystal display device comprising:
providing a liquid crystal material;
adding a liquid crystal compound to the liquid crystal material; and
using the liquid crystal material with the added liquid crystal compound to form a liquid crystal layer having an upper side and a lower side;

wherein the liquid crystal compound improves alignment of liquid crystal molecules of the liquid crystal layer, or enhances orientation of the liquid crystal molecules by being located at either or both of the upper side or lower side of the liquid crystal layer;

wherein the liquid crystal compound is of the formula 1 which has POSS-dendron structure:

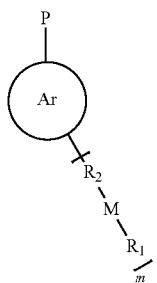

[formula 1]

where Ar is $C_6$-$C_{20}$ aryl,
P is polysilsesquioxane,
Ar and P are linked with oxygen or NCO group,
$R_1$ and $R_2$ are independently $C_1$-$C_{30}$ hydrocarbon,
M is mesogen of compound of the formula 6, and
m is 1-3

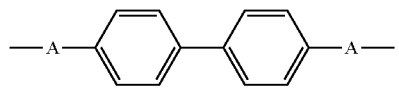

[formula 6]

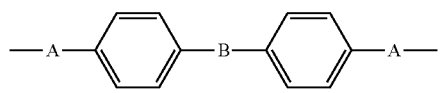

where A is —O—, —COO—, —OCO— or —NHCO—; B is S, O, $N_2$ or $(CH_2)_n$; and n is 1-20.

11. The method of claim 10, wherein the polysilsesquioxane is a POSS-dendron-structured liquid crystal compound of formula 2:

[R—SiO$_{1.5}$]$_n$                      [formula 2]

where R is selected from the group consisting of $C_1$-$C_3$ alkyl, $C_1$-$C_3$ alkenyl, $C_3$-$C_{10}$ cycloalkyl, $C_6$-$C_{15}$ aryl, hydrogen and hydroxyl; and n is an integer of 3-1,000.

12. The method of claim 10, wherein $R_1$ and $R_2$ are independently $C_2$-$C_{30}$ linear or branched alkyl, or $C_2$-$C_{30}$ alkenyl.

13. The method of claim 10, wherein $R_1$ and $R_2$ are independently $C_1$-$C_{30}$ alkylene, $C_1$-$C_{30}$ alkoxy, $C_1$-$C_{30}$ fluoroalkylene, $C_1$-$C_{30}$ ether, $C_1$-$C_{30}$ fluoroether, or —OR$_3$O—, where $R_3$ is $C_1$-$C_{30}$ alkylene or $C_1$-$C_{30}$ fluoroalkylene.

14. The method of claim 10, wherein the compound of formula 1 is selected from the compounds of the following formula 5:

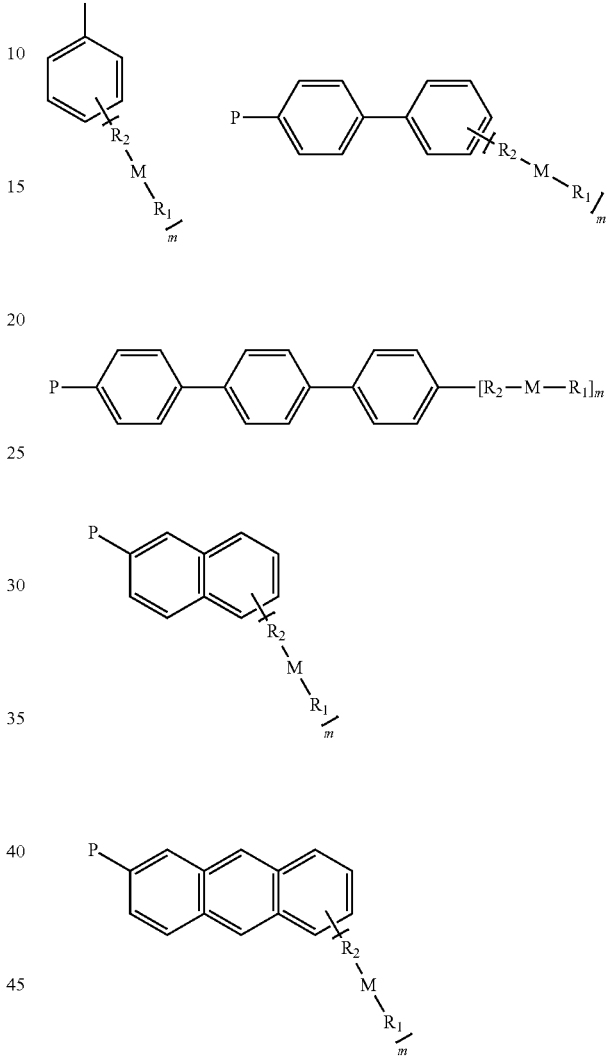

[formula 5]

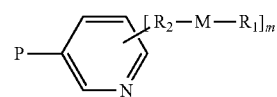

where P is polysilsesquioxane, $R_1$ and $R_2$ are independently $C_1$-$C_{20}$ hydrocarbon, M is mesogen, and m is 1-3.

15. The method of claim 10, wherein the liquid crystal compound of the POSS-dendron structure has a chemical structure of formula 7

[Chemical Formula 7]
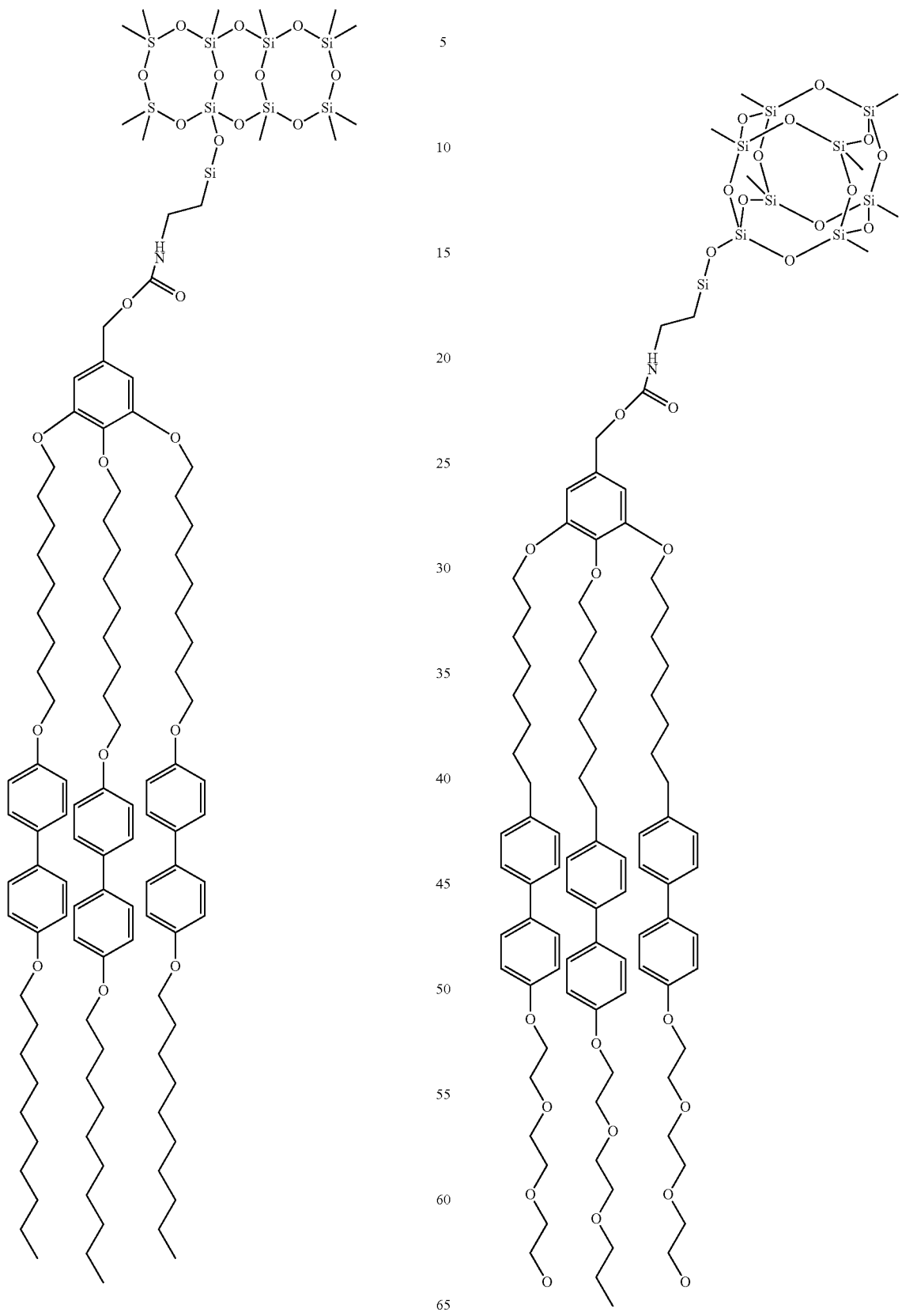

27
-continued
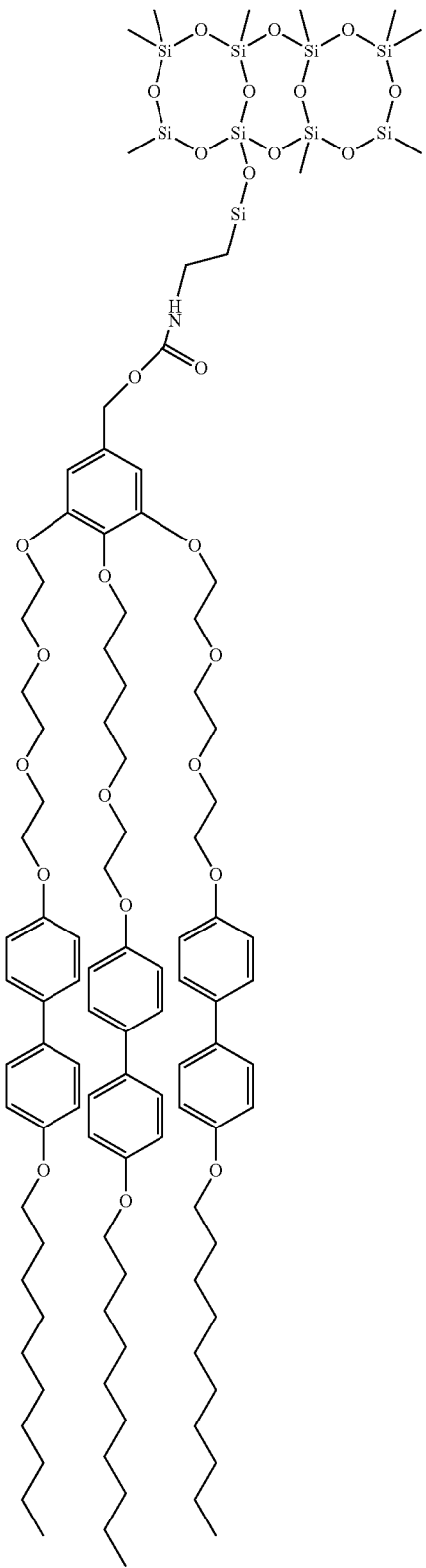
28
-continued
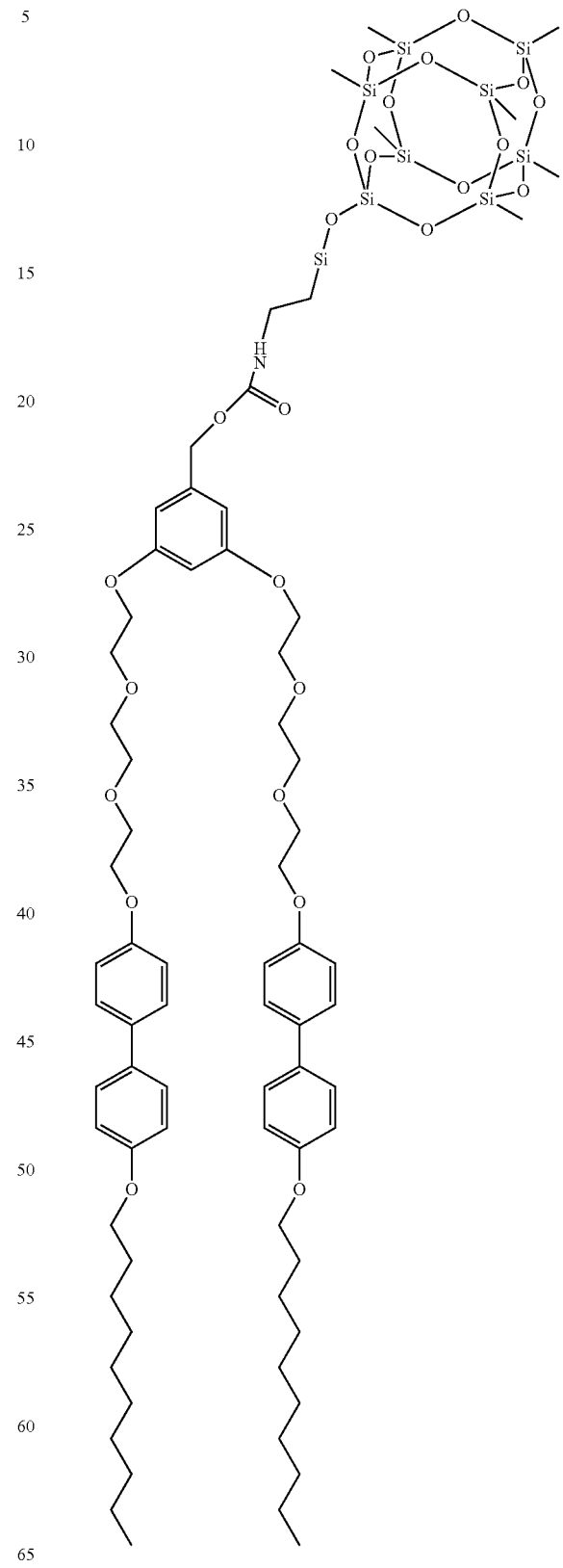

29
-continued
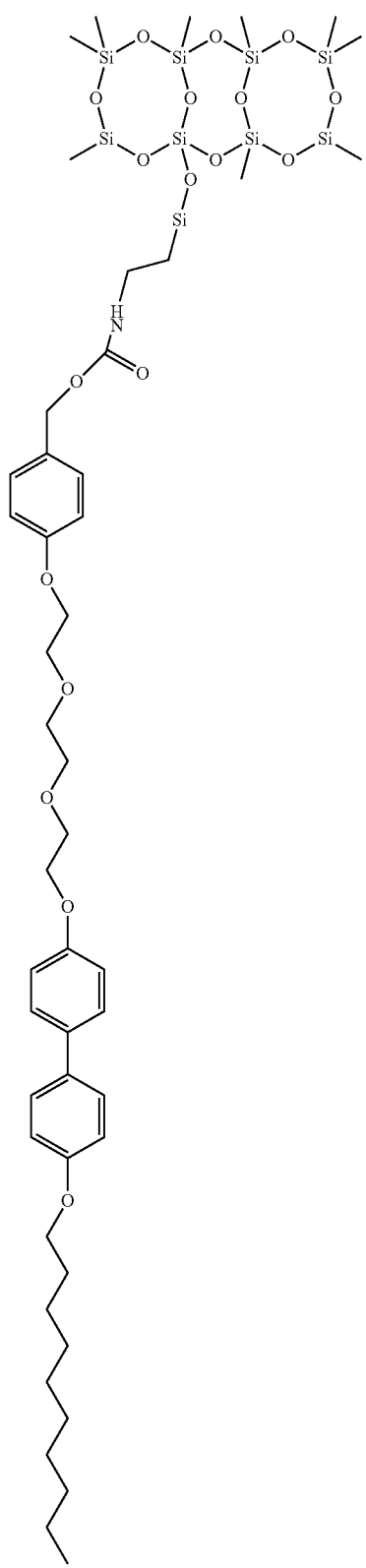
30
-continued
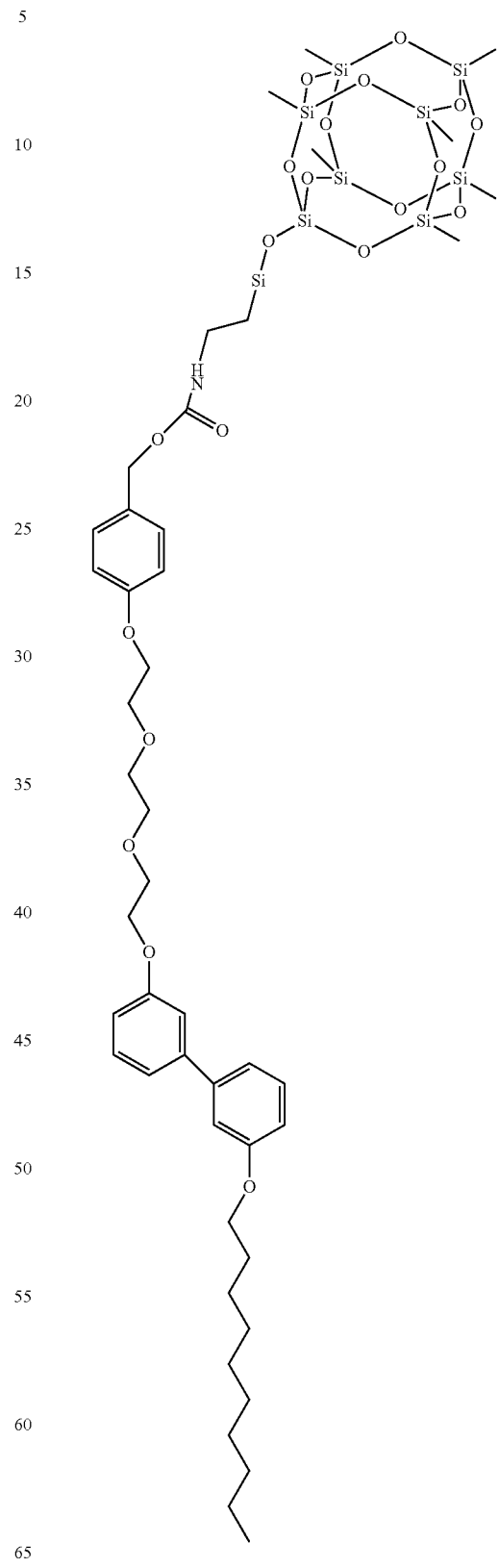

-continued
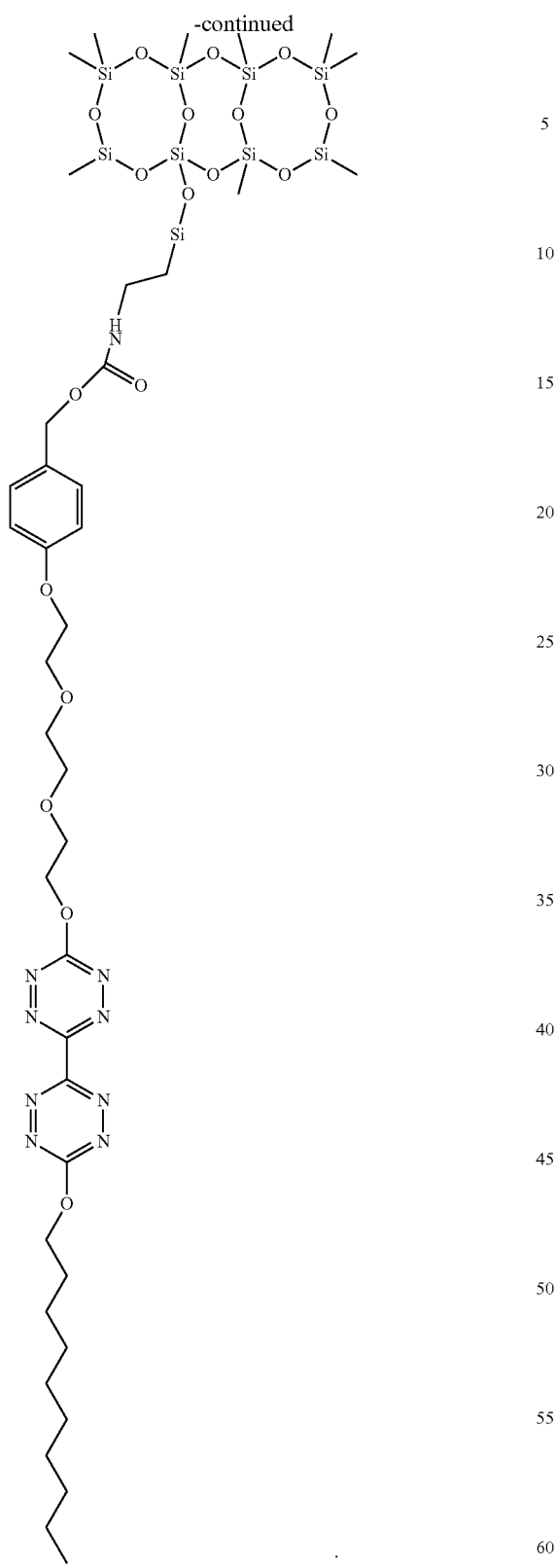
16. The method of claim 10, wherein the liquid crystal compound of the POSS-dendron structure has a weight average molecular weight of 500-3,000 g/mol.
* * * * *